US008313766B2

(12) United States Patent
Chen et al.

(10) Patent No.: US 8,313,766 B2
(45) Date of Patent: Nov. 20, 2012

(54) ORAL ANTIDEPRESSANT FORMULATION WITH REDUCED EXCIPIENT LOAD

(76) Inventors: Andrew Chen, San Diego, CA (US);
Hailiang Chen, San Diego, CA (US);
James Cecil Free, Apex, NC (US);
Majid Keshtmand, Baltimore, MD (US); Mohammed Abdul Rahman, Columbia, MD (US); Sally A. Look, Spicewood, TX (US)

( * ) Notice: Subject to any disclaimer, the term of this patent is extended or adjusted under 35 U.S.C. 154(b) by 133 days.

(21) Appl. No.: 12/860,358

(22) Filed: Aug. 20, 2010

(65) Prior Publication Data

US 2011/0206769 A1    Aug. 25, 2011

Related U.S. Application Data

(60) Provisional application No. 61/301,907, filed on Feb. 5, 2010.

(51) Int. Cl.
*A61K 33/16* (2006.01)

(52) U.S. Cl. ........................................ 424/465; 424/464

(58) Field of Classification Search .......... 424/465–489; 514/434
See application file for complete search history.

(56) References Cited

U.S. PATENT DOCUMENTS

| 6,110,961 | A  | * | 8/2000  | White et al. | 514/434 |
| 7,812,050 | B2 | * | 10/2010 | Brot et al.  | 514/434 |
| 2006/0153918 | A1 | * | 7/2006 | Lerner et al. | 424/473 |

* cited by examiner

*Primary Examiner* — Michael G Hartley
*Assistant Examiner* — Micah-Paul Young
(74) *Attorney, Agent, or Firm* — Womble Carlyle Sandridge & Rice, LLP

(57) ABSTRACT

Provided are methods for reducing the excipient load of pharmaceutical formulations containing 3-fluoro-7-(2,2,2-trifluoroethoxy)phenoxathiin 10,10-dioxide as the active pharmaceutical ingredient, and compositions related thereto. In particular, provided is a pharmaceutical product comprising 3-fluoro-7-(2,2,2-trifluoroethoxy)phenoxathiin 10,10-dioxide and a stabilizer admixed throughout a solid-form unilamellar matrix, wherein the ratio of 3-fluoro-7-(2,2,2-trifluoroethoxy)phenoxathiin 10,10-dioxide to stabilizer ranges from about 2:3 to about 1:10, and related methods of forming the pharmaceutical product.

11 Claims, 2 Drawing Sheets ic ingredient and, more specifically, to pharmaceutical products and methods for reducing the excipient load of pharmaceutical formulations comprising admixed 3-fluoro-7-(2,2,2-trifluoroethoxy)phenoxathiin 10,10-dioxide and a stabilizer.

ORAL ANTIDEPRESSANT FORMULATION WITH REDUCED EXCIPIENT LOAD

CROSS-REFERENCE TO RELATED APPLICATIONS

The present invention claims benefit to U.S. Provisional Application No. 61/301,907, filed Feb. 5, 2010, the content of which is incorporated herein by reference in its entirety.

FIELD OF THE INVENTION

The present invention relates generally to pharmaceutical formulations containing 3-fluoro-7-(2,2,2-trifluoroethoxy)phenoxathiin 10,10-dioxide as the active pharmaceutical ingredient and, more specifically, to pharmaceutical products and methods for reducing the excipient load of pharmaceutical formulations comprising admixed 3-fluoro-7-(2,2,2-trifluoroethoxy)phenoxathiin 10,10-dioxide and a stabilizer.

BACKGROUND

Approximately one-third of the drugs in the United States Pharmacopoeia are water-insoluble or poorly water-soluble. Many currently available injectable formulations of such drugs carry important adverse warnings on their labels that originate from detergents and other agents used for their solubilization. Oral formulations of water-insoluble drugs or compounds with biological uses frequently show poor and erratic bioavailability or require inordinately large quantities of excipient relative to active pharmaceutical ingredient. In addition, water-solubility problems delay or completely block the development of many new drugs and other biologically useful compounds.

SUMMARY

The present invention provides, in one aspect, a pharmaceutical product comprising an admixture of 3-fluoro-7-(2,2,2-trifluoroethoxy)phenoxathiin 10,10-dioxide and a stabilizer. In one embodiment, the ratio of 3-fluoro-7-(2,2,2-trifluoroethoxy)phenoxathiin 10,10-dioxide to stabilizer ranges from about 2:3 to about 1:10. In one embodiment, the 3-fluoro-7-(2,2,2-trifluoroethoxy)phenoxathiin 10,10-dioxide and stabilizer are a solid-form unilamellar matrix. In one embodiment, no more than about 10 percent of the total 3-fluoro-7-(2,2,2-trifluoroethoxy)phenoxathiin 10,10-dioxide changes morphology when the pharmaceutical product is stored for 40 days at 40° C. under 75% relative humidity. In one embodiment, no more than 10 percent of the total 3-fluoro-7-(2,2,2-trifluoroethoxy)phenoxathiin 10,10-dioxide is in crystalline form. In one embodiment, the admixture comprises up to 5%, 10%, 15%, 20%, 25%, 30%, 35% or 40% 3-fluoro-7-(2,2,2-trifluoroethoxy)phenoxathiin 10,10-dioxide.

In another aspect, a process for making a pharmaceutical product of 3-fluoro-7-(2,2,2-trifluoroethoxy)phenoxathiin 10,10-dioxide is provided. In one embodiment, the process comprises the steps of i) dissolving about 2 parts by weight or less of 3-fluoro-7-(2,2,2-trifluoroethoxy)phenoxathiin 10,10-dioxide and about 3 parts by weight of a stabilizer in an organic solvent, and (ii) removing the organic solvent. In another embodiment, the process further comprises the steps of (iii) adding an aqueous liquid to the product of step i) and mixing the resultant suspension, and when the step of adding an aqueous liquid and mixing the resultant suspension is performed, the process includes the step of (iv) subsequently removing the aqueous liquid. In one embodiment, the 3-fluoro-7-(2,2,2-trifluoroethoxy)phenoxathiin 10,10-dioxide in step (i) is Form A.

In another aspect, a pharmaceutical product is provided that comprises a mixture of substantially amorphous 3-fluoro-7-(2,2,2-trifluoroethoxy)phenoxathin 10,10-dioxide as a therapeutically active ingredient and a stabilizer. In one embodiment, the amount of 3-fluoro-7-(2,2,2-trifluoroethoxy)phenoxathin 10,10-dioxide by weight is about 40% or less relative to the amount of weight of 3-fluoro-7-(2,2,2-trifluoroethoxy)phenoxathin 10,10-dioxide plus stabilizer. Embodiments of the pharmaceutical product of the present invention may be no more than 10%, 5%, 2%, 1% or 0.1% of the 3-fluoro-7-(2,2,2-trifluoroethoxy)phenoxathin 10,10-dioxide crystalline. Embodiments of the pharmaceutical product of the present invention may have an area under the curve (AUC) of 3-fluoro-7-(2,2,2-trifluoroethoxy)phenoxathin 10,10-dioxide of at least about 2-fold the AUC of a crystalline form of 3-fluoro-7-(2,2,2-trifluoroethoxy)phenoxathin 10,10-dioxide as determined in a bioavailability assay. Embodiments of the crystalline form of 3-fluoro-7-(2,2,2-trifluoroethoxy)phenoxathin 10,10-dioxide may exhibit a melting point at about 169-175° C., wherein the mixture contains no more than about 2 parts by weight of 3-fluoro-7-(2,2,2-trifluoroethoxy)phenoxathin 10,10-dioxide per about 3 parts by weight of stabilizer. Embodiments of the pharmaceutical product of the present invention may comprise 3-fluoro-7-(2,2,2-trifluoroethoxy)phenoxathin 10,10-dioxide as the sole active ingredient. In other embodiments, the pharmaceutical product of the present invention comprises at least one therapeutically active ingredient. Embodiments of the pharmaceutical product of the present invention may comprise a core which comprises active ingredient or ingredients and an enteric coating surrounding the core. Embodiments of the pharmaceutical products of the present invention achieve plasma levels of phenoxathiin-based MAO-A inhibitor ranging from about 40 ng/ml to about 80 ng/ml.

In another aspect, a pharmaceutical product is provided that comprises an admixture of 3-fluoro-7-(2,2,2-trifluoroethoxy)phenoxathiin 10,10-dioxide as an active ingredient, a stabilizer, and at least one excipient, wherein the ratio of 3-fluoro-7-(2,2,2-trifluoroethoxy)phenoxathiin 10,10-dioxide to the total of the at least one excipient ranges from about 1:1 to about 1:4.

Embodiments of the pharmaceutical product of the present invention may comprise a stabilizer that is a copolymer of vinylpyrrolidone and vinyl acetate, poly(vinylpyrrolidone), hydroxypropyl methylcellulose acetate succinate, hydrogenated phosphatidylcholine, a copolymer of methacrylic acid and ethyl acrylate, or a mixture thereof.

In another aspect, a unit dosage of 3-fluoro-7-(2,2,2-trifluoroethoxy)phenoxathiin 10,10-dioxide is provided that comprises the pharmaceutical products of the present in unit dosages of at least 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 mg of 3-fluoro-7-(2,2,2-trifluoroethoxy)phenoxathiin 10,10-dioxide. In one embodiment, the unit dosage is formulated for oral delivery.

In another aspect, a solid-form unilamellar matrix is provided that comprises an admixture of fluoro-7-(2,2,2-trifluoroethoxy)phenoxathiin 10,10-dioxide as an active ingredient and a stabilizer.

In another aspect, a method of inhibiting monoamine oxidase-A (MAO-A) in a mammal identified as being in need of inhibition of MAO-A is provided that comprises the step of administering a therapeutically effective amount of a pharmaceutical product comprising an admixture of 3-fluoro-7-(2,2,2-trifluoroethoxy)phenoxathiin 10,10-dioxide and a stabilizer, wherein the ratio of 3-fluoro-7-(2,2,2-trifluoroethoxy)phenoxathiin 10,10-dioxide to stabilizer ranges from about 2:3 to about 1:10.

In another aspect, a method of treating or preventing a psychiatric disorder or psychiatric disease is provided that comprises the step of administering a therapeutically effective amount of a pharmaceutical product comprising an admixture of 3-fluoro-7-(2,2,2-trifluoroethoxy)phenoxathiin 10,10-dioxide and a stabilizer, wherein the ratio of 3-fluoro-7-(2,2,2-trifluoroethoxy)phenoxathiin 10,10-dioxide to stabilizer ranges from about 2:3 to about 1:10. In one embodiment, the psychiatric disorder or psychiatric disease is major depressive disorder, dysthymia, childhood depression, atypical depression, bipolar disorder, mania and hypomania, generalized anxiety disorder, social anxiety disorder, obsessive compulsive disorder, panic disorder, post-traumatic stress disorder, premenstrual dysphoric disorder, attention deficit disorder, panic disorder, anergic depression, or treatment-resistant depression.

Combinations of aspects and embodiments form further embodiments of the present invention.

DETAILED DESCRIPTION

Figure 1:
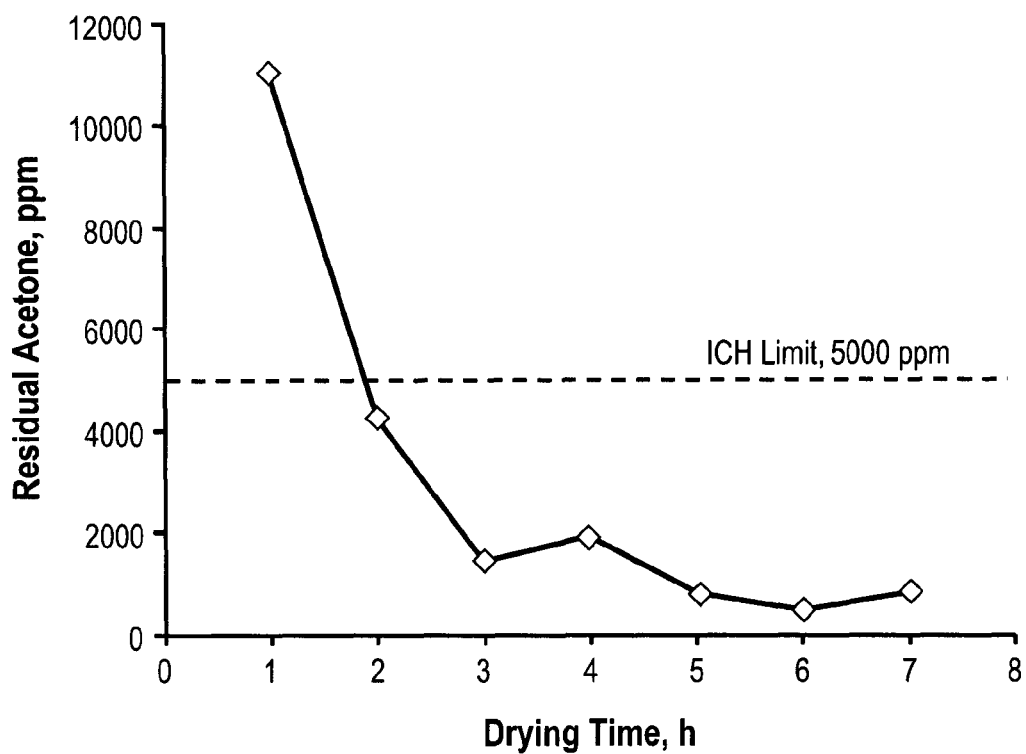
FIG. 1 depicts the amount of residual solvent over time upon drying of a formulation of CX-157/stabilizer.

Provided herein are methods for reducing the excipient load of pharmaceutical formulations containing 3-fluoro-7-(2,2,2-trifluoroethoxy)phenoxathiin 10,10-dioxide as the active pharmaceutical ingredient, and compositions related thereto. Traditional formulation methods have been applied to 3-fluoro-7-(2,2,2-trifluoroethoxy)phenoxathiin 10,10-dioxide, but have resulted in formulations with ratios of nearly 90:1 excipient to 3-fluoro-7-(2,2,2-trifluoroethoxy)phenoxathiin 10,10-dioxide. The product of these traditional formulations requires tableting that would lead to either large unit dosages or a large number of unit dosages required daily, or both. In view of these results, the pharmaceutical composition and related methods provided herein were developed to reduce the excipient load of pharmaceutical formulations containing 3-fluoro-7-(2,2,2-trifluoroethoxy)phenoxathiin 10,10-dioxide in order to provide unit dosage formulations of desired size and quantity for daily administration.

In one embodiment, the pharmaceutical products and methods provided herein allow the CX-157 to be stabilized as essentially an amorphous, i.e., non-crystalline, material, which can improve the bioavailability by oral route of administration without large amounts of excipients. Previously, it had been assumed that large quantities of excipients, and, thus, large dosage forms such as tablets, were necessary to achieve the desired bioavailability of the active ingredient.

CX-157

The active pharmaceutical ingredient of the formulation provided herein is 3-fluoro-7-(2,2,2-trifluoroethoxy)phenoxathiin 10,10-dioxide (also referred to as CX-157 or, as used herein, the active agent), which has the structure:

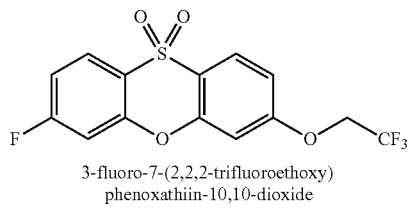

3-fluoro-7-(2,2,2-trifluoroethoxy)
phenoxathiin-10,10-dioxide

CX-157 is a potent and specific monoamine oxidase A (MAO-A) inhibitor which is described in U.S. Pat. No. 6,110,961, U.S. Patent Publication No. 2008/0009542, U.S. Ser. Nos. 61/143,764, and 61/143,767, the entireties of which are incorporated herein by reference. CX-157 is readily soluble in a variety of organic solvents but shows only sparing solubility in water.

As described in more detail herein, in one embodiment the amorphous CX-157 is produced through the Form A polymorph, as described in U.S. Publication No. 2008/0009542, herein incorporated by reference in its entirety. Without being bound by any theory, starting with the "high melt" Form A is believed to enhance the final stability of the amorphous material.

Stabilizer

Stabilizers provided herein are mixed with CX-157 to form a pharmaceutical product that is suitable for further formulation methods (e.g., tableting). While not wishing to be limited to the following explanation, it is believed that the interaction between CX-157 and the stabilizer forms a stable solid, which, under standard long-term storage conditions remains morphologically unchanged such that the morphology of the CX-157 in the solid formulation is substantially not changed over time. Typically the stabilizer is suitable for oral formulations.

Exemplary stabilizers used in accordance with the teachings herein include, but are not limited to, copovidone (copolymer of vinylpyrrolidone and vinyl acetate), povidone (poly(vinylpyrrolidone)), HPMCAS-M (hydroxypropyl methylcellulose acetate succinate), hydrogenated phosphatidylcholine (Phospholipon® 90H), and Eudragit® L100-55 (copolymer of methacrylic acid and ethyl acrylate).

In some embodiments, the stabilizer is readily soluble in at least one solvent in which CX-157 also is soluble. In the formulation methods provided herein, CX-157 and the stabilizer are both dissolved in a solvent, and the solvent is then removed (as described more fully below) to form the pharmaceutical product in which the CX-157 and stabilizer are admixed. Typically, the solubilities of stabilizer and CX-157 in the selected solvent are appropriate for formulation methods. For example, the stabilizer has a solubility of at least, at least about, more than, or more than about, 1 mg/mL, 50 mg/mL, 100 mg/mL, or 500 mg/mL at 60° C. in a solvent in which CX-157 has a solubility of at least 1 mg/mL at 60° C. Typically, the solvent is an organic solvent such as acetone, ethanol, methanol, methylene chloride, and mixtures thereof. In such embodiments, the solubility of the stabilizer in organic solvent is at least, at least about, more than, or more than about 1 mg/mL, 50 mg/mL, 100 mg/mL, or 500 mg/mL at 60° C.

In some embodiments, the melting point of the stabilizer is sufficiently higher than typical ambient or room temperatures such that the stabilizer remains in solid form at typical ambient or room temperatures. As provided herein, in some embodiments this characteristic can permit the stabilizer to maintain the resultant pharmaceutical product in solid form upon admixture with CX-157. As a result, both the pharmaceutical product itself and the CX-157 admixed therein remain substantially morphologically unchanged, even after long-term storage. Typically, the melting point of the stabilizer is at least, at least about, more than, or more than about, 30° C., 40° C., 50° C., 60° C., 70° C., 80° C., 90° C., 100° C., 110° C. 120° C., 130° C., 140° C., 150° C., 160° C., 170° C., or 180° C.

In some embodiments, the stabilizer has limited or no aqueous solubility. In such embodiments, when the pharmaceutical product is stored, contact between the pharmaceutical product and water vapor does not result in dissolution of the stabilizer such that CX-157 is then susceptible to morphological reorganization. In such embodiments, the solubility of the stabilizer in water is no more than, no more than about, less than, or less than about, 500 mg/mL, 250 mg/mL, 125 mg/mL, 75 mg/mL, 30 mg/mL, or 15 mg/mL, 10 mg/mL, 1 mg/mL, 0.5 mg/mL, or 0.1 mg/mL at 60° C.

In other embodiments, the stabilizer is readily soluble under aqueous conditions. In such embodiments, when the pharmaceutical product is administered, contact between CX-157/stabilizer formulation results in efficient dissolution of the stabilizer and CX-157 such that CX-157 is more readily available in the gastrointestinal tract for absorption into the bloodstream. In such embodiments, the solubility of the stabilizer in water is no more than, no more than about, less than, or less than about, 0.5 mg/mL, 1 mg/mL, 5 mg/mL, 10 mg/mL, 50 mg/mL, 100 mg/mL, 200 mg/mL or 500 mg/mL at 60° C.

Other Compounds that can be Mixed in Formulation

Additional compounds can be combined with CX-157 and stabilizer in the pharmaceutical product provided that the formulation and storage properties of the pharmaceutical product remain acceptable in accordance with the guidance provided herein. Examples of suitable additional compounds include any pharmaceutically acceptable excipient such as, for example, vegetable gums, waxes, hydroxypropylmethylcellulose, hydroxypropylcellulose and polyvinylpyrrolidone, carboxymethylcellulose, acacia, gelatin, acetyltriethyl citrate (ATEC), acetyltri-n-butyl citrate (ATBC), aspartame, lactose, alginates, calcium carbonate, carbopol, carrageenan, cellulose, cellulose acetate phthalate, croscarmellose sodium, crospovidone, dextrose, dibutyl sebacate, ethylcellulose, fructose, gellan gum, glyceryl behenate, guar gum, lactose, lauryl lactate, low-substituted hydroxypryopl cellulose (L-HPC), magnesium stearate, maltodextrin, maltose, mannitol, methylcellulose, microcrystalline cellulose (MCC), methacrylate, sodium carboxymethylcellulose, polyvinyl acetate phthalate (PVAP), povidone, shellac, sodium starch glycolate, sorbitol, starch, sucrose, triacetin, triethylcitrate, vegetable based fatty acid, xanthan gum, xylitol; and inert substances such as talc, for example, kaolin, and titanium dioxide, lubricants such as magnesium stearate, finely divided silicon dioxide, crospovidone, and non-reducing sugars. Typically any such additional compounds are suitable for oral formulations.

Method of Preparing Formulation

Provided herein are methods of producing a pharmaceutical product comprising 3-fluoro-7-(2,2,2-trifluoroethoxy)phenoxathiin 10,10-dioxide, by:

i) dissolving about 2 parts by weight or less of the 3-fluoro-7-(2,2,2-trifluoroethoxy)phenoxathiin 10,10-dioxide and 3 parts by weight of a stabilizer in an organic solvent; and ii) removing the organic solvent.

In one embodiment, the process of producing a pharmaceutical product comprising 3-fluoro-7-(2,2,2-trifluoroethoxy)phenoxathiin 10,10-dioxide further comprises the steps of:

iii) adding an aqueous liquid and mixing the resultant suspension; and iv) when iii) is performed, subsequently removing the aqueous liquid.

Dissolution in Organic Solvent

The organic solvent used in step i) is any organic solvent or solvent mixture which does not affect the chemical nature of CX-157 or the stabilizer, in which both CX-157 and the stabilizer are soluble at sufficient concentrations, and which is able to be removed readily, e.g., by evaporation. Typically, the boiling point of the solvent is between, or between about 20° C. and 180° C. Typically, the organic solvent used has low toxicity such that it is an acceptable solvent for pharmaceutical formulations. Particular solvents are alcohols such as methanol, ethanol, 2-methyl-1-propanol, 1-pentanol, 1-propanol, 2-propanol, 1-butanol, 2-butanol, ketones such as acetone, methylethyl ketone, methylisobutyl ketone, methyltert-butyl ketone, and other solvents such as acetic acid, anisole, butyl acetate, terr-butylmethyl ether, cumene, dimethylsufoxide, ethyl acetate, ethyl ether, ethyl formate, formic acid, heptane, isobutyl acetate, ispropyl acetate, methyl acetate and combinations thereof.

The concentration of CX-157 dissolved in the organic solvent can be any amount that provides the desired solid formulation results upon removing the organic solvent from the CX-157/stabilizer solution. Typically, the concentration of CX-157 in the organic solvent is from about 1 mg/mL to about 100 mg/mL.

The concentration of stabilizer dissolved in the organic solvent can be any amount that provides the desired ratio of CX-157 to stabilizer while providing the desired results upon removing the organic solvent from the CX-157/stabilizer solution. Typically, the concentration of stabilizer is from about 1 mg/mL to about 100 mg/mL. One example of CX-157 and stabilizer concentrations is CX-157 at 25 mg/mL and stabilizer at 75 mg/mL, where the stabilizer is copovidone, povidone or HPMCAS-M. Another example of CX-157 and stabilizer concentrations is CX-157 at 35 mg/mL and stabilizer at 65 mg/mL, where the stabilizer is copovidone or povidone. Another example of CX-157 and stabilizer concentrations is CX-157 at 40 mg/mL and stabilizer at 60 mg/mL, where the stabilizer is copovidone.

The dissolving can be conducted at any temperature which does not affect the chemical nature of CX-157 or the stabilizer. The dissolving can be conducted at temperatures above room temperature, such as at 50-70° C. or 55-60° C., optionally followed by cooling. Alternatively, the dissolving can be conducted at room temperature, such as 20-25° C. Dissolving also can be facilitated by any of a variety of mixing methods such as stirring, ultrasound, and use of a bead beater. Those skilled in the art can readily determine a suitable dissolving process according to the solvent to be used, chemical stability of CX-157 and the stabilizer, and desired time frame for conducting the dissolution step.

Removal of Organic Solvent

The organic solvent removal step ii) can be carried out by any of a variety of methods known in the art for solvent removal. For example, the organic solvent can be removed by rotary evaporation or by spray drying. Optimal conditions for conducting the solvent removal can readily be determined by those skilled in the art according to the solvent used, stability of CX-157 and the stabilizer, and desired time frame for conducting the dissolution step. For example, spray drying methods can be performed by spraying in a spray dryer under the conditions: drying air flow rate 70-100 kg/h, inlet temperature 85-125° C., outlet temperature 45-60° C., atomization pressure 0.5-1.5 bar. As a more specific example, spray drying methods can be performed by spraying in a spray dryer under the conditions: drying air flow rate 75-90 kg/h, inlet temperature 90-120° C., outlet temperature 49-56° C., atomization pressure 0.7-1.3 bar. For example, spray drying methods can be performed by spraying in a spray dryer under the conditions: drying air flow rate 80 kg/h, inlet temperature 95° C., outlet temperature 52° C., atomization pressure 1.0 bar.

The further steps for solid drying can be any traditional method known in the art, such as vacuum oven drying. For example, vacuum oven drying can be conducted at 40° C. and about 12-14 mTorr. As will be appreciated by those skilled in the art, the conditions for solvent removal can be modified according to the solvent to be used, chemical stability of CX-157 and the stabilizer, and desired time frame for conducting the solvent removal step.

The resultant solid has substantially all of the organic solvent removed. For purposes herein, substantially all organic solvent removed refers to the solid having no more than, no more than about, less than, or less than about, 10%, 9%, 8%, 7%, 6%, 5%, 4%, 3%, 2.5%, 2%, 1.5%, 1%, 0.9%, 0.8%, 0.7%, 0.6%, 0.5%, 0.4%, 0.3%, 0.2%, 0.1%, or 0.01% organic solvent.

Optional Aqueous Step

In some embodiments the solid can be further treated by contacting the solid with an aqueous liquid. The aqueous liquid can serve to reduce and homogenize the particle size of the solid formed in step ii), referenced herein. The aqueous liquid used in optional step iii) can be an aqueous solution or water itself, particularly de-ionized water. The ratio of the amount of solid treated to the amount of aqueous liquid utilized is typically between 1:1000 to 1:1, 1:500 to 1:2, or 1:20 to 1:4 (w/v). The aqueous liquid contacting step can be performed at any temperature which does not adversely affect the chemical and morphological stability of the solid, and particularly the CX-157 within the solid. In particular, the aqueous liquid contacting step is performed under conditions in which the solid formed in step ii) does not dissolve or change morphologically. For example, the aqueous liquid contacting step can be conducted at room temperature. The particle size reduction and homogenization can be facilitated by any known method, including, for example, using a bead-beater.

The resultant solid particles typically have a mean diameter of no more than, no more than about, less than, or less than about, 1000 nm, 900 nm, 800 nm, 700 nm, 600 nm, 500 nm, 400 nm, 350 nm, 300 nm, 275 nm, 250 nm, 225 nm, 200 nm, 190 nm, 180 nm, 170 nm, 160 nm, 150 nm, 140 nm, 130 nm, 120 nm, 110 nm, or 100 nm.

Aqueous Drying Step

In embodiments that include treatment of the solid by contacting the solid with an aqueous liquid, the aqueous liquid can then be subsequently removed. Any of a variety of known methods for removing aqueous liquids can be used. For example, the aqueous liquid can be removed by lyophilization.

The resultant solid has substantially all of the aqueous liquid removed. For purposes herein, substantially all aqueous liquid removed refers to the solid having no more than, no more than about, less than, or less than about, 10%, 9%, 8%, 7%, 6%, 5%, 4%, 3%, 2.5%, 2%, 1.5%, 1%, 0.9%, 0.8%, 0.7%, 0.6%, 0.5%, 0.4%, 0.3%, 0.2%, 0.1%, or 0.01% aqueous liquid.

Formulation Product

In a preferred embodiment, the pharmaceutical product contains CX-157 and the stabilizer admixed throughout a solid-form unilamellar matrix. The amount of stabilizer present in the pharmaceutical product is at a sufficiently low amount as to permit formation of single unit dosages of a size and a number per daily administration that is acceptable in the art. Typically, the ratio of CX-157 to stabilizer ranges from or from about 1:0.5 to 1:10, 1:0.8 to 1:8, 1:1 to 1:5, 1:1.5 to 1:4, 1:2 to 1:3.5, 1:2.5 to 1:3 or 2:3 to 1:10.

In one embodiment, the pharmaceutical product comprises CX-157, a stabilizer, and at least one excipient, wherein the ratio of CX-157 to the total of the at least one excipient ranges from about 1:1 to about 1:4. In a preferred embodiment, the ratio of CX-157 to the total of the at least one excipient ranges from about 1:2 to about 1:3.

In one embodiment, the pharmaceutical product comprises a 175 mg unit dosage of CX-157. In such an embodiment, the ratio of CX-157 to a primary excipient ranges from about 1:1 to about 7:5. In a preferred embodiment, the ratio of CX-157 to a primary excipient is about 7:6. In one embodiment, the ratio of CX-157 to a secondary excipient ranges from about 1:1 to about 5:3. In a preferred embodiment, the ratio of CX-157 to a secondary excipient is about 5:4.

In an alternative embodiment, the pharmaceutical product comprises a 125 mg unit dosage of CX-157. In such an embodiment, the ratio of CX-157 to a primary excipient ranges from about 0.1:3 to about 2:3. In a preferred embodiment, the ratio of CX-157 to a primary excipient is about 1:3. In one embodiment, the ratio of CX-157 to a secondary excipient ranges from about 0.5:1 to about 4.5:3. In a preferred embodiment, the ratio of CX-157 to a secondary excipient is about 1:1.

In some embodiments, the weight percentage of CX-157 in the combination of CX-157 and stabilizer is no more than or no more than about 40%, 35%, 33%, 30%, 25%, 20%, 15% or 10% (e.g., no more than 40 parts by weight CX-157 per 100 parts of combined weight of CX-157 and stabilizer), where "about" in the present context provides for a variability of no more than $\frac{1}{10}$ of the indicated value (e.g., 40%±4%). Typically the pharmaceutical product is formulated for oral delivery.

In some embodiments, the amount of stabilizer in the solid-form unilamellar matrix of the pharmaceutical product typically is at least, at least about, more than, or more than about 30%, 35%, 40%, 45%, 50%, 55%, 60%, 65%, 70%, 75%, 80%, or 85%, or a range from, between, from about, or between about any of the aforementioned values. When two or more stabilizers are used in the pharmaceutical product, the aforementioned amount of stabilizer refers to the combined amount of all stabilizers in the pharmaceutical product. In some embodiments, the amount of CX-157 in the solid-form unilamellar matrix of the pharmaceutical product typically is at least, at least about, more than, or more than about 5%, 10%, 15%, 20%, 25%, 30%, 35%, 40%, 45%, or 50%, or a range from, between, from about, or between about any of the aforementioned values. In some embodiments, the amount of additional components in the solid-form unilamellar matrix of the pharmaceutical product typically is less than, less than about, no more than, or no more than about 1%, 2%, 3%, 4%, 5%, 7%, 10%, 15%, 20%, 25%, or 30%, or a range from, between, from about, or between about any of the aforementioned values. In some embodiments, the solid-form unilamellar matrix of the pharmaceutical contains no additional components beyond CX-157 and the stabilizer.

In some embodiments, the pharmaceutical product efficiently dissolves in aqueous solutions comparable to a fluid found in the gastrointestinal tract. In particular, the pharmaceutical product dissolves more readily under such conditions compared to a selected crystalline form of CX-157. In such instances, the pharmaceutical product disperses more readily than a selected crystalline form of CX-157, and the CX-157 of the pharmaceutical product is more readily available in the gastrointestinal tract for absorption into the bloodstream than when CX-157 is present in the selected crystalline form of CX-157. In such embodiments, the area under the curve (AUC) for CX-157 in the pharmaceutical product is at least, at least about, more than, or more than about 2-fold, 2.5-fold, 3-fold, 3.5-fold, 4-fold, 4.5-fold, 5-fold, 5.5-fold, or 6-fold the AUC for a selected crystalline form of CX-157. An example of a selected crystal form of CX-157 is crystalline CX-157 having a melting point at about 169-175° C., as described in U.S. Ser. No. 11/773,892, which is herein incorporated by reference. The AUC measurement can be reported at any of a variety of time points such as, for example, 1 hour, 2 hours, 3 hours, 4 hours, 5 hours, 6 hours, 8 hours, 10 hours, 12 hours, 15 hours, 20 hours, 1 day, 2 days or 3 days. The conditions under which the AUC measurements can be performed can be any method established in the art as providing a reliable model for bioavailability of a pharmaceutical product.

In some embodiments, the pharmaceutical product has limited or no aqueous solubility. As a result, when the pharmaceutical product is stored, contact between the pharmaceutical product and water does not result in dissolution of the pharmaceutical product such that CX-157 is then susceptible to morphological reorganization. In such embodiments, the solubility of the pharmaceutical product in water is no more than, no more than about, less than, or less than about, 500 mg/mL, 250 mg/mL, 175 mg/mL, 125 mg/mL, 75 mg/mL, 30 mg/mL, or 15 mg/mL, 10 mg/mL, 1 mg/mL, 0.5 mg/mL, or 0.1 mg/mL at 60° C.

In some embodiments, the melting point of the pharmaceutical product is sufficiently higher than typical ambient or room temperatures that the pharmaceutical product remains in solid form at these temperatures. This characteristic permits the pharmaceutical product to remain in solid form throughout its shelf storage. As a result, both the pharmaceutical product itself and the CX-157 admixed therein remain substantially morphologically unchanged, even after long-term storage. In such embodiments, the melting point of the pharmaceutical product is at least, at least about, more than, or more than about, 30° C., 40° C., 50° C., 60° C., 70° C., 80° C., 90° C., 100° C., 110° C. 120° C., 130° C., 140° C., 150° C., 160° C., 170° C., or 180° C.

Use of the term substantially morphologically unchanged, as it applies to the pharmaceutical product or CX-157 refers to the condition in which the morphological nature of the solid does not change above a tolerated amount over a given storage period. For example, the morphological nature of the solid does not change above a tolerated amount when stored at 25° C. for 1 month, 2 months, 3 months, 4 months, 5 months or 6 months (i.e., 30-180 days). In another example, the morphological nature of the solid does not change above a tolerated amount when stored at 40° C. for about 1 month, 2 months, 3 months, 4 months, 5 months or 6 months (i.e., 30-180 days). The storage conditions under which the morphology is substantially unchanged can include moisture in the ambient environment. For example, the storage conditions under which the morphology is substantially unchanged can have 90%, 80%, 75%, 70%, 60%, 50%, 40%, 30%, 20%, 10%, or 0%, relative humidity.

The tolerated amount of morphological change of the pharmaceutical product or CX-157 refers to the maximum amount of pharmaceutical product or CX-157 that can change morphology, such as, change from amorphous to any crystalline form, change from one crystalline form (including co-crystalline form) to a different crystalline form (including co-crystalline form), or change from solid to liquid or solute form. The tolerated amount of morphological change of the pharmaceutical product or CX-157 is typically no more than, no more than about, less than, or less than about, 10%, 9%, 8%, 7%, 6%, 5%, 4%, 3%, 2.5%, 2%, 1.5%, 1%, 0.9%, 0.8%, 0.7%, 0.6%, 0.5%, 0.4%, 0.3%, 0.2%, 0.1%, or 0.01% morphological change of the pharmaceutical product or CX-157. Morphological change can be measured by any of a variety of known methods, including, for example, differential scanning calorimetry and powder x-ray diffraction.

In some embodiments, the CX-157 in the pharmaceutical product is substantially non-crystalline. As provided herein, typically pharmaceutical formulation methodologies avoid formation of non-crystalline or amorphous forms of an active pharmaceutical ingredient because such forms are considered unstable during storage. In contrast to the general thinking in the art, this embodiment of the pharmaceutical product provided herein is able to maintain a non-crystalline form that is stable over time and is suitable for storage. The phrase substantially non-crystalline CX-157 refers to the total amount of CX-157 in the pharmaceutical product being no more than, no more than about, less than, or less than about, 10%, 9%, 8%, 7%, 6%, 5%, 4%, 3%, 2.5%, 2%, 1.5%, 1%, 0.9%, 0.8%, 0.7%, 0.6%, 0.5%, 0.4%, 0.3%, 0.2%, 0.1%, or 0.01% crystalline. Crystal forms of CX-157 are known in the art, as taught in U.S. Ser. No. 11/773,892, which is incorporated herein by reference. Crystallinity of CX-157 can be measured by any of a variety of known methods, including, for example, differential scanning calorimetry and powder x-ray diffraction.

In some embodiments, the amount of moisture uptake under any one or more of the above-described storage conditions by the pharmaceutical product or a unit dosage form formulated therefrom is no more than, no more than about, less than, or less than about, 20%, 19%, 18%, 17%, 16%, 15%, 14%, 13%, 12%, 11%, 10%, 9%, 8%, 7%, 6%, 5%, 4%, 3%, 2.5%, 2%, 1.5%, 1%, 0.9%, 0.8%, 0.7%, 0.6%, 0.5%, 0.4%, 0.3%, 0.2%, or 0.1%.

In some embodiments, the pharmaceutical product contains substantially no liposomes in the solid-form unilamellar matrix containing the stabilizer and CX-157. Although some stabilizers known in the art can be used to prepare liposomes that contain active pharmaceutical ingredients, it is believed that at least some of the methods and stabilizers provided herein for forming the pharmaceutical product yield combinations of stabilizer and CX-157 which are not in liposome form. Liposomes are vesicular structures of aligned hydrophobic and hydrophilic groups of molecules, and can often have dynamic, liquid- or gel-like structures at room temperature. In contrast, the pharmaceutical products provided herein have melting points well above room temperature and remain morphologically stable under standard storage conditions, permitting the CX-157 contained therein to also maintain good morphological stability over time. The phrase substantially no liposomes in the solid-form unilamellar matrix refers to the pharmaceutical product containing no more than, no more than about, less than, or less than about, 10%, 9%, 8%, 7%, 6%, 5%, 4%, 3%, 2.5%, 2%, 1.5%, 1%, 0.9%, 0.8%, 0.7%, 0.6%, 0.5%, 0.4%, 0.3%, 0.2%, 0.1%, or 0.01% (w/w) liposomes. Any of the methods for identifying and characterizing liposomes known in the art can be used to assess the amount of liposomes present in the pharmaceutical product.

Typically, the pharmaceutical product contains substantially no organic solvent. For purposes herein, substantially no organic solvent refers to the pharmaceutical product having no more than, no more than about, less than, or less than about, 10%, 9%, 8%, 7%, 6%, 5%, 4%, 3%, 2.5%, 2%, 1.5%, 1%, 0.9%, 0.8%, 0.7%, 0.6%, 0.5%, 0.4%, 0.3%, 0.2%, 0.1%, or 0.01% organic solvent.

Typically, the pharmaceutical product contains substantially no aqueous liquid. For purposes herein, substantially no aqueous liquid refers to the pharmaceutical product having no more than, no more than about, less than, or less than about, 10%, 9%, 8%, 7%, 6%, 5%, 4%, 3%, 2.5%, 2%, 1.5%, 1%, 0.9%, 0.8%, 0.7%, 0.6%, 0.5%, 0.4%, 0.3%, 0.2%, 0.1%, or 0.01% aqueous liquid.

Dosage Form

The instant pharmaceutical products may be administered to the patient by any suitable means. Non-limiting examples of methods of administration include, among others, (a) administration though oral pathways, which administration includes administration in capsule, tablet, granule, spray, syrup, or other such forms; (b) administration through non-oral pathways such as rectal, vaginal, intraurethral, intraocular, intranasal, or intraauricular, which administration includes administration as an aqueous suspension, an oily preparation or as a drip, spray, suppository, salve, or ointment; (c) administration via injection, subcutaneously, intraperitoneally, intravenously, intramuscularly, intradermally, intraorbitally, intracapsularly, intraspinally, or intrasternally, including infusion pump delivery; (d) administration locally such as by injection directly in the renal or cardiac area, e.g., by depot implantation; as well as (e) administration topically; as deemed appropriate by those of skill in the art for bringing the compound of the invention into contact with living tissue.

Also provided herein are unit dosages containing the pharmaceutical product. In a preferred embodiment, a unit dosage provided herein is a discrete vessel containing the pharmaceutical product, including, but not limited to, a tablet, pill, dragee, capsule, caplet, gelcap, or suppository, typically formulated for oral or other gastro-intestinal tract-mediated ingestion by a subject to be treated.

In some embodiments, the amount of CX-157 in a unit dosage is at least, at least about, more than, or more than about 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 mg, or a range from, between, from about, or between about any of the aforementioned values. In some embodiments, the amount of stabilizer or combination of stabilizers in a unit dosage is at least, at least about, more than, or more than about 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 325, 350, 375, 400, 450, 500, 550, 600, 650, 700, 750, 800, 850, 900, 950, or 1000 mg, or a range from, between, from about, or between about any of the aforementioned values. Typically, the amount of CX-157 in a unit dosage is the amount required to constitute or constitute about 1/10, 1/9, 1/8, 1/7, 1/6, 1/5, 1/4, 1/3, one half, or a full daily dose of CX-157, or a range from, between, from about, or between about any of the aforementioned values. That is, typically the number of unit dosages required for delivery of a daily dose to a subject is 10 or less, 5 or less, 4 or less, 3 or less (TID), 2 or less (BID), or one daily (QD).

The unit dosages can contain any of a variety of additional coatings known in the art, particularly oral formulation coatings. Such additional coatings include, but are not limited to, lubricant coating, enteric coating, sustained release coating, or controlled release coating. Examples of various coatings containing CX-157 are provided in PCT/US10/20468 and PCT/US10/20459, the entireties of which are incorporated herein by reference.

The unit dosage is formed according to any of a variety of methods known in the art, such as tableting methods. As provided herein, the pharmaceutical product shows good compressibility for core formation, thus facilitating tableting and other such methodologies. Typically, the pharmaceutical product is sieved, e.g., using a 120 mesh and then further treated in tableting or other unit dosage formation methods.

Oral Dosage Formulations

Oral dosage formulations containing CX-157 can be configured to: control location in the digestive system of release and absorption of CX-157; control the rate of release of CX-157; or both control location in the digestive system of release and absorption of CX-157 and control the rate of release of CX-157. Such oral dosage formulations can contain a core that contains CX-157, and also at least one additional layer, such as an enteric coating layer, a sustained release layer, or both.

Figure 2:
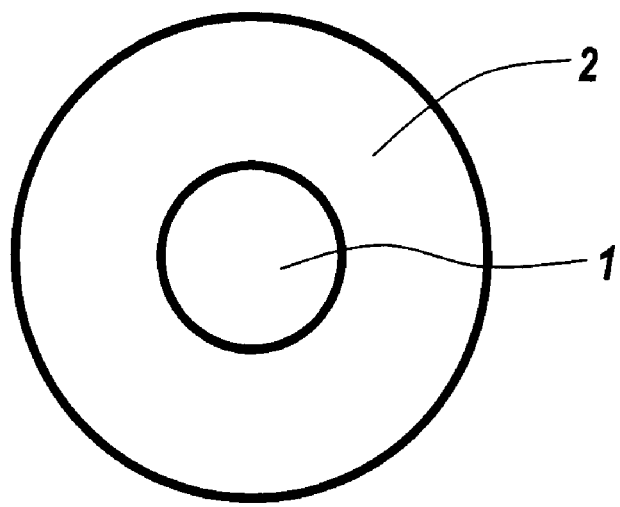
FIGS. 2(a) and 2(b) depict schematic examples of oral formulations containing CX-157.
Figure 2:
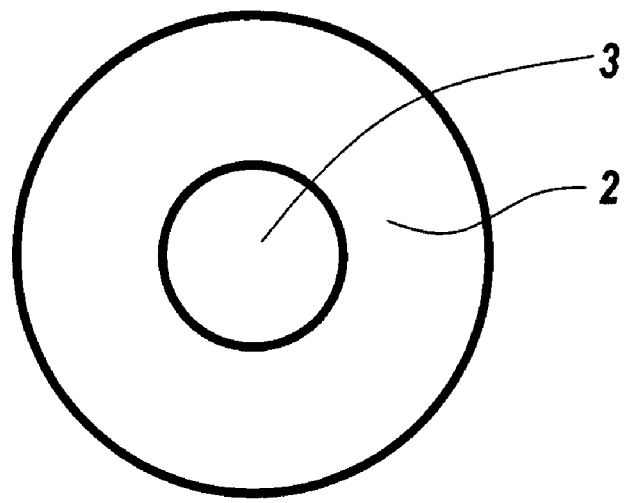

In some embodiments, such presentations comprise one or more of: (a) a traditional core containing CX-157 and one or more pharmaceutical excipients; (b) a sustained release layer containing CX-157 and one or more sustained release excipients; (c) a separating layer; (d) an enteric layer comprising hydroxypropylmethylcellulose acetate succinate (HPMCAS) and a pharmaceutically acceptable excipient; and (e) a finishing layer. In some embodiments, a sustained release layer is present. In some embodiments, an enteric layer is present. In some embodiments, both a sustained release layer and an enteric layer are present. In some such embodiments, the core comprises an inert bead on which the CX-157 is deposited as a layer comprising the one or more pharmaceutical excipients. In some embodiments, the product is a tablet or capsule or a core sheathed in an annular body. In some embodiments, such presentations contain about 50 to 500 milligrams of CX-157. Example embodiments are depicted in FIG. 2, where FIG. 2(a) depicts a preparation containing a traditional core 1 containing CX-157, and an enteric coat 2; and FIG. 2(b) depicts a preparation containing a sustained release layer 3 containing CX-157, and an enteric coat 2.

As used herein, all expressions of percentage, ratio, and proportion will be in weight units unless otherwise stated. Expressions of proportions of the enteric product will refer to the product in dried form, after the removal of the water in which many of the ingredients are dissolved or dispersed.

The term sugar refers to a sugar other than a reducing sugar. A reducing sugar is a carbohydrate that reduces Fehling's (or Benedict's) or Tollens' reagent. All monosaccharides are reducing sugars as are most disaccharides with the exception of sucrose. One common binding or filling agent is lactose which is particularly useful for tablets since lactose compresses well and is a cost-efficient diluent and binder. Lactose, however, is a reducing sugar that potentially interacts with the active ingredient at both at room temperature and under accelerated stability conditions (heat). Therefore, avoidance of lactose and other reducing sugars from formulations comprising the active ingredient may be important. As discussed below, sucrose is a particularly preferred sugar.

The Core

A particular core for the pellet is typically prepared by applying a layer containing active ingredient (CX-157) to an inert core. Such inert cores are conventionally used in pharmaceutical science, and are readily available. A particular core is one prepared from starch and sucrose, for use in confectionery as well as in pharmaceutical manufacturing. Cores of any pharmaceutically acceptable excipient, however, can be used, including, for example, microcrystalline cellulose (MCC), vegetable gums, or waxes. The primary characteristic of the inert core is to be inert, with regard both to the active ingredient and the other excipients in the pellet and with regard to the subject who will ultimately ingest the pellet.

The size of the cores depends on the desired size of the pellet to be manufactured. In general, pellets can be as small as 0.1 mm, or as large as 2 mm. Particular cores are from about 0.3 to about 0.8 mm, in order to provide finished pellets in the size range of from about 0.5 to about 1.5 mm in diameter. For instance, the cores can be of a reasonably narrow particle size distribution, in order to improve the uniformity of the various coatings to be added and the homogeneity of the final product. For example, the cores can be specified as being of particle size ranges such as from 18 to 20 U.S. mesh, from 20 to 25 U.S. mesh, from 25 to 30 U.S. mesh, or from 30 to 35 U.S. mesh to obtain acceptable size distributions of various absolute sizes.

The amount of cores to be used can vary according to the weights and thicknesses of the added layers. In general, the cores comprise from about 10 to about 70 percent of the product. More particularly, the charge of cores represents from about 15 to about 45 percent of the product.

When manufacture of the pellet begins with inert cores, the active ingredient can be coated on the cores to yield a final drug concentration of about 10 to about 25 percent of the product, in general. The amount of active ingredient depends on the desired dose of the drug and the quantity of pellets to be administered. The active ingredient can be present in at least, or at least about, more than, or more than about, 10 mg, 15 mg, 20 mg, 25 mg, 30 mg, 40 mg, 50 mg, 60 mg, 70 mg, 80 mg, 90 mg, 100 mg, 125 mg, 150 mg, 175 mg, or 200 mg. The active ingredient can be present in up to, or up to about, less than, or less than about, 25 mg, 30 mg, 40 mg, 50 mg, 60 mg, 70 mg, 80 mg, 90 mg, 100 mg, 125 mg, 150 mg, 175 mg, 200 mg, 250 mg, 300 mg, 350 mg, 400 mg, 450 mg, 500 mg, 600 mg, 700 mg, 800 mg, 900 mg or 1000 mg. Particular ranges include about 50 mg to about 500 mg, or from about 100 mg to about 200 mg.

A convenient manner of coating the cores with active ingredient is the "powder coating" process where the cores are moistened with a sticky liquid or binder, active ingredient is added as a powder, and the mixture is dried. Such a process is regularly carried out in the practice of industrial pharmacy, and suitable equipment is known in the art.

Such equipment can be used in several steps of the present process. This process can be conducted in conventional coating pans similar to those employed in sugar coating processes. This process can be used to prepare pellets.

Alternately, the present product can be made in fluidized bed equipment (using a rotary processor), or in rotating plate equipment such as the Freund CF-Granulator (Vector Corporation, Marion, Iowa). The rotating plate equipment typically consists of a cylinder, the bottom of which is a rotatable plate. Motion of the mass of particles to be coated is provided by friction of the mass between the stationary wall of the cylinder and the rotating bottom. Warm air can be applied to dry the mass, and liquids can be sprayed on the mass and balanced against the drying rate as in the fluidized bed case.

In some embodiments, a powder coating is applied. In such embodiments, the mass of pellets can be maintained in a sticky state, and the powder to be adhered to them, can be added continuously or periodically and adhered to the sticky pellets. When all of such active has been applied, the spray can be stopped and the mass allowed to dry in the air stream. It can be appropriate or convenient to add some inert powders to the active ingredient.

Additional solids can be added to the layer with active ingredient. These solids can be added to facilitate the coating process as needed to aid flow, reduce static charge, aid bulk buildup and form a smooth surface. Inert substances such as talc, kaolin, and titanium dioxide, lubricants such as magnesium stearate, finely divided silicon dioxide, crospovidone, and non-reducing sugars, e.g., sucrose, can be used. The amounts of such substances are in the range from about a few tenths of 1% of the product up to about 20% of the product. Such solids are typically of fine particle size, e.g., less than 50 micrometers, to produce a smooth surface.

The active ingredient can be made to adhere to the cores by spraying a pharmaceutical excipient which is sticky and adherent when it is wet, and dries to a strong, coherent film. Those skilled in the art are aware of and conventionally use many such substances, most of them polymers. Particular such polymers include hydroxypropylmethylcellulose (i.e., hypromellose), hydroxypropylcellulose and polyvinylpyrrolidone. Additional such substances include methylcellulose, carboxymethylcellulose, acacia and gelatin, for example. The amount of the adhering excipient can be in the range from about 4% to about 12% of the product, and depends, in large part, on the amount of active to be adhered to the core.

The active ingredient can also be built up on the cores by spraying a slurry comprising active suspended in a solution of the excipients of the active layer, dissolved or suspended in sufficient water to make the slurry sprayable. Such a slurry can be milled through a machine adapted for grinding suspension in order to reduce the particle size of active. Grinding in suspension form can be desirable because it avoids dust generation and containment problems which arise in grinding dry powder drugs. A particular method for applying this suspension is the pharmaceutical fluidized bed coating device, such as the Wurster column, which consists of a vertical cylinder with an air-permeable bottom and an upward spraying nozzle close above the bottom, or a downward-spraying nozzle mounted above the product mass. The cylinder is charged with particles to be coated, a sufficient volume of air is drawn through the bottom of the cylinder to suspend the mass of particles, and the liquid to be applied is sprayed onto the mass. The temperature of the fluidizing air is balanced against the spray rate to maintain the mass of pellets or tablets at the desired level of moisture and stickiness while the coating is built up.

On the other hand, the core can comprise a monolithic particle in which the active ingredient is incorporated. Such cores can be prepared by the granulation techniques which are wide spread in pharmaceutical science, particularly in the preparation of granular material for compressed tablets. The cores can be prepared by mixing the active into a mass of pharmaceutical excipients, moistening the mass with water or a solvent, drying, and breaking the mass into sized particles in the same size range as described above for the inert cores. This can be accomplished via the process of extrusion and marumerization.

The core for the pellet can also be prepared by mixing active with conventional pharmaceutical ingredients to obtain the desired concentration and forming the mixture into cores of the desired size by conventional procedures, including but not limited to the process of R. E. Sparks et al., U.S. Pat. Nos. 5,019,302 and 5,100,592, incorporated by reference herein.

Sustained Release

In some embodiments, the product is formulated so as to achieve plasma levels of CX-157 ranging from about 40 ng/ml to about 80 ng/ml. Also provided are oral pharmaceutical dosage forms comprising CX-157 and adapted to retard release of CX-157 in the digestive tract.

Sustained-release pharmaceutical formulations can be configured in a variety of dosage forms such as, for example tablets and beads. Such dosage forms can contain a variety of fillers and excipients, such as retardant excipients (also referred to a release modifiers) and can be made in a variety of ways. Those skilled in the art can determine the appropriate configuration by routine experimentation guided by the descriptions provided herein.

Sustained-release pharmaceutical formulations can contain fillers. Examples of suitable fillers include, but are not limited to, methylcellulose, including that sold under the tradename METHOCEL®, hydroxypropyl methylcellulose (HPMC), hydroxypropylcellulose (HPC), corn starch, polyvinyl alcohol (PVA), polyvinylpyrrolidone (PVP), or cross-linked PVP.

Sustained-release pharmaceutical formulations can contain excipients. Examples of suitable excipients include, but are not limited to, acetyltriethyl citrate (ATEC), acetyltri-n-butyl citrate (ATBC), aspartame, lactose, alginates, calcium carbonate, carbopol, carrageenan, cellulose, cellulose acetate phthalate, croscarmellose sodium, crospovidone, dextrose, dibutyl sebacate, ethylcellulose, fructose, gellan gum, glyceryl behenate, guar gum, lactose, lauryl lactate, low-substituted hydroxypryopl cellulose (L-HPC), magnesium stearate, maltodextrin, maltose, mannitol, methylcellulose, microcrystalline cellulose (MCC), methacrylate, sodium carboxymethylcellulose, polyvinyl acetate phthalate (PVAP), povidone, shellac, sodium starch glycolate, sorbitol, starch, sucrose, triacetin, triethylcitrate, vegetable based fatty acid, xanthan gum, or xylitol.

The active ingredient can be present in at least, or at least about, more than, or more than about, 10 mg, 15 mg, 20 mg, 25 mg, 30 mg, 40 mg, 50 mg, 60 mg, 70 mg, 80 mg, 90 mg, 100 mg, 125 mg, 150 mg, 175 mg, or 200 mg. The active ingredient can be present in up to, or up to about, less than, or less than about, 25 mg, 30 mg, 40 mg, 50 mg, 60 mg, 70 mg, 80 mg, 90 mg, 100 mg, 125 mg, 150 mg, 175 mg, 200 mg, 250 mg, 300 mg, 350 mg, 400 mg, 450 mg, 500 mg, 600 mg, 700 mg, 800 mg, 900 mg or 1000 mg. Particular ranges include about 50 mg to about 500 mg, or from about 100 mg to about 200 mg.

In preferred embodiments, the sustained-release pharmaceutical formulation comprises an active ingredient, methylcellulose and microcrystalline cellulose (MCC). In some embodiments, the formulation comprises, for example, from about 30%, 40%, or 50%, to about 80% or 90% active ingredient by weight. In some embodiments, the formulation comprises about 0.1%, 0.5%, 1%, 3%, 5%, 10% or or 20% active ingredient by weight. Preferably, the active ingredient is present at a percentage of about 55%, 60%, 65%, or 70% by weight. In other preferred embodiments, the formulation comprises about 95% active ingredient.

The balance of ingredients in the sustained-release active ingredient pharmaceutical formulation can be chosen, for example, from modified polysaccharides such as, for example, methylcellulose (MC) and microcrystalline cellulose (MCC). In some embodiments, the formulation comprises between about 3% to about 99.9% microcrystalline cellulose by weight. In certain embodiments, the formulation comprises about 3% MCC. In other embodiments, the formulation comprises about 5% MCC. In further embodiments, the formulation comprises about 10% MCC. In yet other embodiments, the formulation comprises about 30% MCC. In further embodiments, the formulation comprises about 50% MCC.

In some embodiments, the sustained-release pharmaceutical formulation comprises about 0% to about 40% MC. In certain embodiments, the formulation comprises about 3% MC. In other embodiments, the formulation comprises about 5% MC. In further embodiments, the formulation comprises about 10% MC. In yet other embodiments, the formulation comprises about 30% MC. In further embodiments, the formulation comprises about 40% MC. In some embodiments, the formulation comprises about 95% active ingredient and the remaining 5% is divided between MC and MCC.

The dissolution rate of the sustained-release pharmaceutical formulation determines how quickly active ingredient becomes available for absorption into the blood stream and therefore controls the bioavailability of active ingredient. Dissolution rate is dependent on the size and the composition of the dosage form. In some embodiments, the dissolution rate of the formulation can be by changed by altering the additional components of the formulation. Disintegrants, such as starch or corn starch, or crosslinked PVPs, can be used to increase solubility when desired. Solubilizers can also be used to increase the solubility of the formulations. In some embodiments, alternative binders, such as, for example, hydroxypropylmethyl cellulose (HPMC), hydroxypropyl cellulose (HPC), methyl cellulose (MC), PVP, gums, or xanthine can be used to increase the dissolution rate.

In some embodiments, the dissolution rate of the formulation can be decreased by adding components that make the formulation more hydrophobic. For example, addition of polymers such as ethylcelluloses, wax, or magnesium stearate decreases the dissolution rate.

In some embodiments, the dissolution rate of the sustained-release pharmaceutical formulation is formulated so as to control the plasma levels of active ingredient. For example, the sustained-release pharmaceutical formulation can be formulated so as to achieve plasma levels of active ingredient that are, for example, at least, or at least about, more than, or more than about, 5 ng/ml, 10 ng/ml, 15 ng/ml, 20 ng/ml, 25 ng/ml, 30 ng/ml, 40 ng/ml, 50 ng/ml, 60 ng/ml, 70 ng/ml, 80 ng/ml, 90 ng/ml, or 100 ng/ml. The sustained-release pharmaceutical formulation can be formulated so as to achieve plasma levels of active ingredient that are, for example, up to, or up to about, less than, or less than about, 25 ng/ml, 30 ng/ml, 40 ng/ml, 50 ng/ml, 60 ng/ml, 70 ng/ml, 80 ng/ml, 90 ng/ml, 100 ng/ml, 125 ng/ml, 150 ng/ml, 175 ng/ml, 200 ng/ml, 250 ng/ml, 300 ng/ml, 350 ng/ml, 400 ng/ml, 450 ng/ml, or 500 ng/ml. Particular ranges are from about 10 ng/ml to about 150 ng/ml, from about 20 ng/ml to about 100 ng/ml, or from about 40 ng/ml to about 80 ng/ml. In one embodiment, such ranges can be favorable for achieving therapeutic levels of active ingredient without causing sufficient inhibition of MAO inhibition in the digestive tract and liver so as to cause the so-called "cheese effect."

In some embodiments, the dissolution rate of the sustained-release pharmaceutical formulation is such that about 25% of the active ingredient in the dosage form is dissolved within the first hour, about 60% of the active ingredient is dissolved within the first 6 hours, about 80% of the active ingredient is dissolved within the first 9 hours, and substantially all of the active ingredient is dissolved within the first 12 hours. In other embodiments, the dissolution rate of the sustained-release pharmaceutical formulation is such that about 35% of the active ingredient in the dosage form is dissolved within the first hour, about 85% of the active ingredient is dissolved within the first 6 hours, and substantially all of the active ingredient is dissolved within the first 9 hours. In yet other embodiments, the dissolution rate of the sustained-release pharmaceutical formulation in the dosage form is such that about 45% of the active ingredient is dissolved within the first hour, and substantially all of the active ingredient is dissolved within the first 6 hours.

The dissolution rate of the formulation can also be slowed by coating the dosage form. Examples of coatings include sustained-release polymers.

The sustained-release pharmaceutical formulation can take about, for example, from 2, 4, 6, or 8 hours to about 15, 20, or 25 hours to dissolve. Preferably, the formulation has a dissolution rate of from about 3, 4, 5, or 6 to about 8, 9, or 10 hours.

Another embodiment provides a method of preparing sustained-release pharmaceutical formulation. The method comprises mixing active ingredient with an excipient or filler or a combination thereof to form a mixture, and forming a suitable dosage form (e.g., tablet, bead, etc.) from the mixture. In some embodiments, the method of preparing the formulation further comprises adding another excipient or filler or a combination thereof to the mixture prior to forming the dosage form. The filler and excipient are as described herein. In an embodiment, the active ingredient is mixed with the excipient or filler or a combination thereof to form a wet mixture. The wet mixture can then be formed into particles or beads, which can then be dried. The dried product can then be tableted or placed into a gelatin capsule for oral delivery.

In an embodiment, the sustained-release pharmaceutical formulation is in the form of beads. In some embodiments, the beads comprise active ingredient and a filler. In other embodiments, the beads further comprise an excipient. In some embodiments, the excipient or filler or a combination thereof are in polymeric form.

As used herein, "beads" can be, for example, spheres, pellets, microspheres, particles, microparticles, or granules. The beads can have any desired shape. The shape can be, for example, spherical, substantially spherical, rod-like, cylindrical, oval, elliptical, or granular. The size and shape of the bead can be modified, if desired, to alter dissolution rates. The beads can be coated or can be uncoated. The beads can be formed into a capsule for oral delivery, a tablet, or any other desired solid oral dosage form, with or without other ingredients.

In an embodiment, a pharmaceutical formulation comprises a bead that comprises sustained-release active ingredient and a filler. In some embodiments, the bead further comprises an excipient. In some embodiments, the filler is a polymer. In some embodiments the excipient is a polymer. In some embodiments, the filler is selected from the group consisting of methylcellulose, hydroxypropyl methylcellulose (HPMC), hydroxypropylcellulose (HPC), corn starch, polyvinyl alcohol (PVA), polyvinylpyrrolidone (PVP), and crosslinked PVP. In some embodiments, the excipient is selected from the group consisting of acetyltriethyl citrate (ATEC), acetyltri-n-butyl citrate (ATBC), aspartame, lactose, alginates, calcium carbonate, carbopol, carrageenan, cellulose, cellulose acetate phthalate, croscarmellose sodium, crospovidone, dextrose, dibutyl sebacate, ethylcellulose, fructose, gellan gum, glyceryl behenate, guar gum, lactose, lauryl lactate, low-substituted hydroxypropyl cellulose (L-HPC), magnesium stearate, maltodextrin, maltose, mannitol, methylcellulose, microcrystalline cellulose (MCC), methacrylate, sodium carboxymethylcellulose, polyvinyl acetate phathalate (PVAP), povidone, shellac, sodium starch glycolate, sorbitol, starch, sucrose, triacetin, triethylcitrate, vegetable based fatty acid, xanthan gum, and xylitol. In some embodiments the bead comprises active ingredient, methylcellulose and microcrystalline cellulose. In some embodiments, the bead comprises from about 0.1% to about 95% active ingredient by weight. In some embodiments, the bead comprises between about 3% to about 99.9% microcrystalline cellulose by weight. In some embodiments, the bead comprises about 0% to about 40% methylcellulose by weight.

Separating Layer

The separating layer between the active-containing core and the enteric layer is not required, but is a particular feature of the formulation. The functions of the separating layer, if desired, are to provide a smooth base for the application of the enteric layer, to prolong the resistance of the pellet to acid conditions, and/or to improve stability by inhibiting any interaction between the drug and the enteric polymer in the enteric layer.

The smoothing function of the separating layer is purely mechanical, the objective of which is to improve the coverage of the enteric layer and to avoid thin spots in the enteric layer, caused by bumps and irregularities on the core. Accordingly, the more smooth and free of irregularities the core can be made, the less material is needed in the separating layer, and the need for the smoothing characteristic of the separating layer can be avoided entirely when the active is of extremely fine particle size and the core is made as close as possible to truly spherical.

When a pharmaceutically acceptable non-reducing sugar is added to the separating layer, the pellet's resistance to acid conditions can be markedly increased. Accordingly, such a sugar can be included in the separating layer applied to the cores, either as a powdered mixture, or dissolved as part of the sprayed-on liquid. A sugar-containing separating layer can reduce the quantity of enteric polymer required to obtain a given level of acid resistance. Use of less enteric polymer can reduce both the materials cost and processing time, and also can reduce the amount of polymer available to react with active. The inhibition of any core/enteric layer interaction is mechanical. The separating layer physically keeps the components in the core and enteric layers from coming into direct contact with each other. In some cases, the separating layer can also act as a diffusional barrier to migrating core or enteric layer components dissolved in product moisture. The separating layer can also be used as a light barrier by opacifying it with agents such as titanium dioxide or iron oxides.

In general, the separating layer can include coherent or polymeric materials, and finely powdered solid excipients which constitute fillers. When a sugar is used in the separating layer, the sugar is applied in the form of an aqueous solution and constitutes part of or the whole of the coherent material which sticks the separating layer together. In addition to or instead of the sugar, a polymeric material can also be used in the separating layer. For example, substances such as hydroxypropylmethylcellulose, polyvinylpyrrolidone, or hydroxypropylcellulose can be used in small amounts to increase the adherence and coherence of the separating layer.

A filler excipient also can be used in the separating layer to increase the smoothness and solidity of the layer. Substances such as finely powered talc or silicon dioxide are universally accepted as pharmaceutical excipients and can be added as is convenient in the circumstances to fill and smooth the separating layer.

In general, the amount of sugar in the separating layer can be in the range of from about 2% to about 10% of the product, when a sugar is used at all, and the amount of polymeric or other sticky material can be in the range of from about 0.1 to about 5%. The amount of filler, such as talc, can be in the range of from about 5 to about 15%, based on final product weight.

The separating layer can be applied by spraying aqueous solutions of the sugar or polymeric material, and dusting in the filler as has been described in the preparation of an active layer. The smoothness and homogeneity of the separating layer can be improved, however, if the filler is thoroughly dispersed as a suspension in the solution of sugar and or polymeric material, and the suspension is sprayed on the core and dried, using equipment as described above in the preparation of cores with active layers.

Enteric Layer

In some embodiments, the presentation comprises an enteric coating. Enteric pharmaceutical presentations of CX-157 can serve to protect the MAO receptors from binding to CX-157 in the stomach to thereby limit dangerous food reactions or decrease the requirement for strict dietary restrictions by virtue of reducing release of the active ingredient and thereby reducing the degree to which CX-157 blocks MAO receptors from binding dietary tyramine. In some embodiments, such presentations comprise CX-157 and are adapted to retard or inhibit the release of CX-157 in the stomach.

The enteric layer is comprised of an enteric polymer, which can be chosen for compatibility with the active ingredient. The polymer can be one having only a small number of carboxylic acid groups per unit weight or repeating unit of the polymer. A particular enteric polymer is hydroxypropylmethylcellulose acetate succinate (HPMCAS), which product is defined as containing not less than 4% and not more than 28% of succinoyl groups, which are the only free carboxylic groups in the compound. See Japanese Standards of Pharmaceutical Ingredients 1991, page 1216-21, Standard No. 19026. HPMCAS is available from Shin-Etsu Chemical Co., Ltd., Tokyo, Japan, under the trademark AQOAT. It is available in two particle size grades and three molecular weight ranges. For example, the L grade, having number average molecular weight of 93,000 can be used.

Enteric polymers can be applied as coatings from aqueous suspensions, from solutions in aqueous or organic solvents, or as a powder. One skilled in the art will be able to select from known solvents or methods or a combination thereof, as desired.

The enteric polymer can also be applied according to a method described by Shin-Etsu Chemical Co. Ltd. (Obara, et al., Poster PT6115, AAPS Annual Meeting, Seattle, Wash., Oct. 27-31, 1996). In this method, when the enteric polymer is applied as a powder the enteric polymer is added directly in the solid state to the tablets or pellets while plasticizer is sprayed onto the tablets or pellets simultaneously. The deposit of solid enteric particles is then turned into a film by curing. The curing is done by spraying the coated tablets or pellets with a small amount of water and then heating the tablets or pellets for a short time. This method of enteric coating application can be performed employing the same type of equipment as described above in the preparation of cores with active ingredient layers.

When the enteric polymer is applied as an aqueous suspension, a problem in obtaining a uniform, coherent film often results. In instances in which this problem may arise, a fine particle grade can be used or the particles of polymer can be ground to an extremely small size before application. It is possible either to grind the dry polymer, as in an air-impaction mill or to prepare the suspension and grind the polymer in slurry form. Slurry grinding is generally preferable, particularly since it can be used also to grind the filler portion of the enteric layer in the same step. In some embodiments, it is advisable to reduce the average particle size of the enteric polymer to the range from about 1 micrometer to about 5 micrometers, particularly no larger than 3 micrometers.

When the enteric polymer is applied in the form of a suspension, the suspension is typically maintained homogeneous. Such precautions include maintaining the suspension in a gently stirred condition, but not stirring so vigorously as to create foam, and assuring that the suspension does not stand still in eddies in nozzle bodies, for example, or in over-large delivery tubing. Frequently, polymers in suspension form will agglomerate if the suspension becomes too warm, and the critical temperature can be as low as 30° C. in individual cases. Since spray nozzles and tubing are exposed to hot air in the usual fluid bed type equipment, care must be taken to assure that the suspension is kept moving briskly through the equipment to cool the tubing and nozzle. When HPMCAS is used, in particular, it is advisable to cool the suspension below 20° C. before application, to cool the tubing and nozzle by pumping a little cold water through the tubing and nozzle before beginning to pump the suspension, and to use supply tubing with as small a diameter as the spray rate will allow so that the suspension can be kept moving rapidly in the tubing.

In one embodiment, one can apply the enteric polymer as an aqueous solution whenever it is possible to do so. In the case of HPMCAS, dissolution of the polymer can be obtained by neutralizing the polymer, particularly with ammonia. Neutralization of the polymer can be obtained merely by adding ammonia, preferably in the form of aqueous ammonium hydroxide to a suspension of the polymer in water; complete neutralization results in complete dissolution of the polymer at about pH 5.7-5.9. Good results are also obtained when the polymer is partially neutralized by adding less than the equivalent amount of ammonia. In such case, the polymer which has not been neutralized remains in suspended form, suspended in a solution of neutralized polymer. The particle size of the polymer can be controlled when such a process is to be used. Use of neutralized polymer more readily provides a smooth, coherent enteric layer than when a suspended polymer is used, and use of partially neutralized polymer provides intermediate degrees of smoothness and coherency. Particularly when the enteric layer is applied over a very smooth separating layer, excellent results can be obtained from partially neutralized enteric polymer.

The extent of neutralization can be varied over a range without adversely affecting results or ease of operation. For example, the extent of neutralization can range from about 25% to about 100% neutralization. Another particular condition is from about 45% to about 100% neutralization, and another condition is from about 65% to about 100%. Still another particular manner of neutralization is from about 25% to about 65% neutralized. It may be found, however, that the enteric polymer in the resulting product, after drying, is neutralized to a lesser extent than when applied. When neutralized or partially neutralized HPMCAS is applied, the HPMCAS in the final product can be from about 0% to about 25% neutralized, more particularly from about 0% to about 15% neutralized.

A plasticizer can be used with enteric polymers for improved results. In the case of HPMCAS, a particular plasticizer can be triethyl citrate, used in an amount up to about 15%-30% of the amount of enteric polymer in aqueous suspension application. When a neutralized HPMCAS is employed, either lower levels or no plasticizer can be required. Minor ingredients, such as antifoam, suspending agents when the polymer is in suspended form, and surfactants to assist in smoothing the film, are also commonly used. For example, silicone anti-foams, surfactants such as polysorbate 80, sodium lauryl sulfate and suspending agents such as carboxymethylcellulose and vegetable gums, can commonly be used at amounts in the general range up to 1% of the product.

Usually, an enteric layer is filled with a powdered excipient such as talc, glyceryl monostearate or hydrated silicon dioxide to build up the thickness of the layer, to strengthen it, to reduce static charge, and to reduce particle cohesion. Amounts of such solids in the range of from about 1% to about 10% of the final product can be added to the enteric polymer mixture, while the amount of enteric polymer itself can be in the range from about 5% to about 25%, more particularly, from about 10% to about 20%.

Application of the enteric layer to the pellets follows the same general procedure previously discussed, using fluid bed type equipment with simultaneous spraying of enteric polymer solution or suspension and warm air drying. Temperature of the drying air and the temperature of the circulating mass of pellets are typically kept in the ranges advised by the manufacturer of the enteric polymer.

Provided herein are formulations engineered to initiate drug release in the middle to lower portions of the small intestine, with a delayed release time of greater than, for example, approximately 1 hour, 1.25 hours, 1.5 hours, 1.75 hours or 2 hours after dosing. Such pharmaceutical formulations are manufactured in such a way that the product passes unchanged through the stomach of the patient, and dissolves and releases the active ingredient when it leaves the stomach and enters the middle and lower portions of the small intestine. Such formulations can be in tablet or pellet form, where the active ingredient is in the inner part of the tablet or pellet and is enclosed in a film or envelope (i.e., the "enteric coating"). The enteric coating is insoluble in acid environments, such as the stomach, but is soluble in near-neutral environments such as the small intestine. The instant enteric coating-containing formulations avoid much of the drug competition with dietary tyramine for MAO-A since dietary tyramine is rapidly absorbed and metabolized in the stomach and upper portion of the small intestine and the liver with an average Tmax of 1.25 hours. In this regard, human plasma pharmacokinetic data of tyramine, administered with food in a capsule, in an oral dose of 200 mg demonstrated a rapid absorption of tyramine with a Tmax achieved within 1.25 hours and non-detectable levels observed 3-4 hrs after dosing.

Finishing Layer

A finishing layer over the enteric layer is not necessary in every case, but can improve the elegance of the product and its handling, storage and machinability and can provide further benefits as well. The simplest finishing layer is simply a small amount, about less than 1% of an anti-static ingredient such as talc or silicon dioxide, simply dusted on the surface of the pellets. Another simple finishing layer is a small amount, about 1%, of a wax such as beeswax melted onto the circulating mass of pellets to further smooth the pellets, reduce static charge, prevent any tendency for pellets to stick together, and increase the hydrophobicity of the surface.

More complex finishing layers can constitute a final sprayed-on layer of ingredients. For example, a thin layer of polymeric material such as hydroxypropylmethylcellulose or polyvinylpyrrolidone, in an amount such as from about 2% up to about 10%, can be applied. The polymeric material can also carry a suspension of an opacifier, a bulking agent such as talc, or a coloring material, particularly an opaque finely divided color agent such as red or yellow iron oxide. Such a layer quickly dissolves away in the stomach, leaving the enteric layer to protect the active ingredient, but provides an added measure of pharmaceutical elegance and protection from mechanical damage to the product.

Finishing layers to be applied to the present product are of essentially the same types commonly used in pharmaceutical science to smooth, seal and color enteric products, and can be formulated and applied in the usual manners.

Methods of Use

The pharmaceutical products provided herein can be used in methods of treating medical, psychiatric or neurological conditions or disorders. In one embodiment, the methods include administering a MAO-A-inhibiting effective amount or therapeutically effective amount of a pharmaceutical product comprising 3-fluoro-7-(2,2,2-trifluoroethoxy)phenoxathiin 10,10-dioxide as an active ingredient and a stabilizer admixed throughout a solid-form unilamellar matrix to a mammal, particularly a human, in need for the treatment of medical, psychiatric or neurological conditions and disorders. In one embodiment, the ratio of 3-fluoro-7-(2,2,2-trifluoroethoxy)phenoxathiin 10,10-dioxide to stabilizer ranges is from about 2:3 to about 1:10. As used herein, the therapeutically effective amount is an amount effective to achieve the intended purpose. The therapeutically effective amount can depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

In one embodiment, the pharmaceutical products provided herein can be used to treat medical, psychiatric or neurological conditions and disorders including, but are not limited to, depressive disorders (major depressive disorder, dysthymia, childhood depression, atypical depression, bipolar disorder, mania and hypomania), anxiety disorders (generalized anxiety disorder, social anxiety disorder, phobias, obsessive compulsive disorder, panic disorder, post-traumatic stress disorder), premenstrual dysphoric disorder (also known as premenstrual syndrome), attention deficit disorder (with and without hyperactivity), Intermittent Explosive Disorder, Alzheimer's disease, Parkinson's disease, hyperactivity, conduct disorder, narcolepsy, obesity, eating disorders such as anorexia nervosa and bulimia nervosa, drug withdrawal syndromes and drug dependence disorders, including dependence from alcohol, opioids, amphetamines, cocaine, tobacco, and cannabis (marijuana), melancholia, panic disorder, anergic depression, treatment-resistant depression, headache, acute and chronic pain syndromes, as exemplified by fibromyalgia, chronic low back pain, trigeminal neuralgia, visceral pain syndromes, such as irritable bowel syndrome, noncardiac chest pain, functional dyspepsia, interstitial cystitis, essential vulvodynia, urethral syndrome, orchialgia, temperomandibular disorder, atypical face pain, migraine headache, and tension headache; functional somatic disorders, for example, chronic fatigue syndrome, and other conditions in which alteration of MAO-A activity could be of therapeutic value.

The following examples are included for illustrative purposes only and are not intended to limit the scope of the invention.

EXAMPLES

Example 1

Solvent Selection for Formulation of CX-157

The criteria for solvents for use in preparing a CX-157 formulation include high solubility for CX-157, low boiling point and high vapor pressure for easy removal by vacuum, and safety (class 3 or 2 in FDA Q3C guidance).

Procedure

Ethanol, acetone and methylene chloride were selected and tested as candidate solvents. CX-157 solubility in the solvent was performed using a test tube method. A specific amount of CX-157 (Form A: disclosed in U.S. Pat. Pub. No. 2008/0009542 herein incorporated by reference in it entirety) was added into 1 mL test solvent and the sample was agitated vigorously by a Beadbeater (BB). If CX-157 was completely soluble in 1 mL of test solvent, additional CX-157 was added until excess solid was present. The solubility (mg/mL) of CX-157 was calculated by the amount (mass) of CX-157 added to the test solvent (1 mL). The solubility of CX-157 in ethanol, acetone and methylene chloride is shown in Table 1. Acetone had the highest solubility of the solvents tested with a solubility of from about 60 mg/mL to about 80 mg/mL at room temperature.

TABLE 1

| Solvent | Solubility (mg/mL) |
| --- | --- |
| Ethanol | Less than 10 mg/mL at 60° C. |
| Acetone | 60~80 mg/mL at room temperature |
| Methylene chloride | Less than 20 mg/mL at room temperature |

Example 2

Thermal Stability Analysis of Formulation of CX-157 with Primary Stabilizer

A CX-157-Primary Stabilizer complex was prepared by dissolving CX-157 (crystal Form A: disclosed in U.S. Pat. Pub. No. 2008/0009542 herein incorporated by reference in it entirety) and Phospholipon® 90H (PL90H; Phosphatidylcholine, hydrogenated) in acetone, then removing the solvent by Speedvac to obtain a solid complex. For comparative purposes, a physical mixture was prepared by mixing solid CX-157 (Form A) with Phospholipon® 90H. The CX-157 and Phospholipon® 90H were combined in a variety of wt/wt ratios: CX-157/PL90H solid complex (1:1 by wt), CX-157/PL90H solid complex (1:3 by wt), CX-157/PL90H physical mixture (1:1 by wt).

The CX-157 (Form A) exhibited an endothermic "melting" peak at 170.4° C. and heat of fusion of about 107 microvolt-seconds/milligrams (µV-s/mg). The CX-157/PL90H physical mixture showed the same CX-157 (Form A) endothermic melting peak and a heat of fusion similar to CX-157 (Form A). Compared to CX-157 (Form A), the CX-157/PL90H solid complex (1:1 and 1:3 ratios) had an endothermic peak at about 159° C. with a significantly reduced heat of fusion, as shown in Table 2. In contrast to CX-157 crystal Form A and the physical mixture of CX-157/PL90H (1:1 by wt), the CX-157/PL90H solid complex (1:1 by wt) had a heat of fusion of 38.7 µV-s/mg. Additionally, the CX-157/PL90H solid complex (1:3 by wt) had a heat of fusion of 10.2 µV-s/mg. These differences can be attributed to a disappearance of the original CX-157 crystal Form A with an overall reduction of crystallinity in the solid complex.

TABLE 2

| | CX-157/PL90H wt ratio | | |
| --- | --- | --- | --- |
| | 1:0 (100% CX-157) | 1:1 | 1:3 |
| PL90H | 107 | 38.7 | 10.2 |

Heat of Fusion (µV-s/mg).

Example 3

Analysis of Melting Point and Heat of Fusion of CX-157:PL90H Complexes in Varying Ratios The CX-157:PL90H complex of varying ratios were formed by preparing a 50 mg/mL CX-157 stock solution in acetone, preparing a 500 mg/mL PL90H stock solution in ethanol (heat at 60° C. to dissolve) and then combining 0.4 mL of the CX-157 stock solution with an appropriate amount of the PL90H stock solution in a vial (2 mL) to provide a mixture with the desired ratios as shown in Table 3.

TABLE 3

| | (mg/vials) | | | | | | | | | |
| --- | --- | --- | --- | --- | --- | --- | --- | --- | --- | --- |
| | Mg | | | | | | | | | |
| vial | F-1 | F-15 | F-11 | F-16 | F-17 | F-18 | F-19 | F-20 | F-21 | F-12 |
| CX-157 | 20 mg | 20 mg | 20 mg | 20 mg | 20 mg | 20 mg | 20 mg | 20 mg | 20 mg | 20 mg |
| PL90H | 20 mg | 40 mg | 60 mg | 80 mg | 100 mg | 120 mg | 140 mg | 160 mg | 180 mg | 200 mg |
| CX-157:PL90H | 1:1 | 1:2 | 1:3 | 1:4 | 1:5 | 1:6 | 1:7 | 1:8 | 1:9 | 1:10 |

The vials were each heated at 60° C. for 30 min to obtain a clear solution, then the solvent was removed by SpeedVac (solvent to less than 2%). To each vial was added 0.8 mL deionized-water and then placed on the BB for 120 seconds to obtain a suspension. The water was removed on a lyophilizer. The melting point and the heat of fusion were measured for the CX-157:PL90H complexes formed by the aqueous suspension method as shown in Table 4.

TABLE 4

| | Peak 1 (120-150° C.) | | Peak 2 (150-160° C.) | | Peak 3 (160-170° C.) | |
| --- | --- | --- | --- | --- | --- | --- |
| Sample (PL90H:CX-157) | Melting point (° C.) | Heat of fusion (µV-s/mg) | Melting point (° C.) | Heat of fusion (µV-s/mg) | Melting point (° C.) | Heat of fusion (µV-s/mg) |
| PL90H | 124.4 | 50.6 | / | / | / | / |
| CX-157 | / | / | / | / | 169.4 | 120 |

TABLE 4-continued

| Sample (PL90H:CX-157) | Peak 1 (120-150° C.) | | Peak 2 (150-160° C.) | | Peak 3 (160-170° C.) | |
|---|---|---|---|---|---|---|
| | Melting point (° C.) | Heat of fusion (µV-s/mg) | Melting point (° C.) | Heat of fusion (µV-s/mg) | Melting point (° C.) | Heat of fusion (µV-s/mg) |
| (1:1) | 128.1 | 3.4 | / | / | 160.0 | 24.2 |
| (2:1) | 130.8 | 5.33 | 157.6 | 10.2 | 168.1 | 2.87 |
| (3:1) | 131.6 | 6.07 | 151.9 | 9.84 | / | / |
| (4:1) | 131.9 | 5.41 | 152.1 | 9.59 | / | / |
| (5:1) | 132.5 | 5.92 | 153.4 | 4.36 | / | / |
| (6:1) | 133.6 | 8.15 | / | / | / | / |
| (7:1) | 135.3 | 7.54 | / | / | / | / |
| (8:1) | 133.9 | 9.50 | / | / | / | / |
| (9:1) | 133.5 | 5.28 | / | / | / | / |
| (10:1) | 134.3 | 6.62 | / | / | / | / |

Particles of complexes with a CX-157-to-PL90 ratio from 1:1 to 1:10 produced by the aqueous suspension method, exhibited new endothermic peaks (Peak 1 and Peak 2) with significantly reduced melting point and heat of fusion. Between 1:3 and 1:10 (CX-157-to-PL90 ratio), the CX-157 original crystalline peak (169° C.) disappeared. The CX-157 (Form A) original crystalline peak (169° C.) was completely absent at a 1:3 complex (CX-157-to-PL90 ratio). Additionally, the 1:3 complex (CX-157-to-PL90 ratio) formed nanoparticles (200-240 nm).

Example 4

Preparation of CX-157/PL90H (1:3, w/w) Complex by Spray Drying and Vacuum Drying Processes Vacuum Drying (RV) Preparation of CX-157/PL90H (1:3; w/w) Complex The CX-157 and PL90H in the appropriate ratio were placed in a round bottom glass flask. A mixture of solvent (acetone/ethanol=3/2 v/v,) was combined with the CX-157 and PL90H and heated to 55-60° C. (bath temp) to obtain a clear solution. The solvent was removed, until the residual solvent is about 10% w/w of the net weight, under reduced pressure (RotaVap: Buchi R-205; 200-250 mTorr) to provide a slightly yellow dry mass. The dry mass was transferred onto a tray and then the tray is placed into a vacuum oven. The dry mass was heated under vacuum (12-14 mTorr) at 40° C. to further remove solvent until less than 0.5-1% by thermogravimetric analysis (TGA). The solid was passed a 100-mesh sieve (150 µm) and was then stored dry in a sealed container.

Spraying Drying (SD) Preparation of CX-157/PL90H (1:3; w/w) Complex

The CX-157 and PL90H in the appropriate ratio were placed in a glass bottle. A mixture of solvent (acetone/ethanol=3/2 v/v,) was combined with the CX-157 and PL90H and heated to 55-60° C. (bath temp) to obtain a clear solution. The solution was maintained at 55-60° C. then spraying was accomplished (Yamato Spray Dryer Model Pulvis GB22) using the following conditions:

a. Flow rate: 4-5 mL/min b. Drying air flow rate: 0.3-0.4 m$^3$/min c. Inlet temp: 85° C.

d. Outlet temp: 55-59° C.

The dry mass was transferred onto a tray and then the tray was placed into a vacuum oven. The dry mass was heated under vacuum (12-14 mTorr) at 40° C. to further remove solvent until less than 2% by TGA by thermogravimetric analysis (TGA). The solid was passed a 100-mesh sieve (150 µm) and was then stored dry in a sealed container.

A comparison of the solid formed by vacuum drying (RV) and spray drying (SD) is shown in Table 5. The solids formed by the RV and SD processes take on about 7-8% water when exposed to 70% relative humidity.

TABLE 5

| Powder properties | SD | RV |
|---|---|---|
| Assay (%, w/w) | 23.7 ± 0.2 | 22.1 ± 0.4 |
| Appearance | Off white and fluffy | Off white |
| Bulk density (g/mL) | 0.19 | 0.45 |
| Particle size | 5-20 micron | 20~100 micron |
| TGA analysis | solvent residues: ~1.9% | solvent residues: ~0.6% |

Example 5

DSC Method for Differentiating Crystalline and Amorphous CX-157 in the Complex

The CX-157/PL90H (1:3; w/w) complex formed by the RV method was spiked with 5%, 10%, 20%, and 50% crystalline CX-157 (Form A). For comparative purposes 100% CX-157/PL90H (1:3; w/w) complex and 100% crystalline CX-157 (Form A) were included in the analysis, as shown in Table 6.

TABLE 6

Endothermic events and heat of fusion

| | Peaks related to PL90H or complex | | | | Peak related to crystalline CX-157 | |
|---|---|---|---|---|---|---|
| | 120-140° C. | | 150-165° C. | | | |
| Sample ID | MP (° C.) | Heat Fusion (μV-s/mg) | MP (° C.) | Heat Fusion (μV-s/mg) | MP (° C.) | Heat Fusion (μV-s/mg) |
| 100% CX-157/ PL90H complex | 122.6; 136.2 | 56.8 | 156.3 | 4.07 | No peak | No peak |
| 5% Crystalline | 121.6; 135.5; | 53.2 | 154.0 | 1 | 164.8 | 3.1 |
| 10% Crystalline | 122.3; 135.6; | 50.7 | 162.2 | 2.5 | 165.4 | 2.7 |
| 20% Crystalline | 122.0; 135.7 | 54.0 | No peak | No peak | 166.1 | 11.0 |
| 50% Crystalline | 121.1; 135.5 | 46.4 | No peak | No peak | 169.2 | 25.4 |
| 100% Crystalline | No peak | No peak | No peak | No peak | 169.5 | 110 |

The sample with 100% CX-157/PL90H (1:3; w/w) complex had no peaks related to 100% crystalline CX-157 (Form A). Peaks related to crystalline CX-157 (Form A) were detected in all spiked samples. The crystalline CX-157 (Form A) had a distinctive melting event at 169° C. The CX-157/PL90H (1:3; w/w) complex had 2-3 endothermic events up to 165° C., well separated from the crystalline CX-157 (Form A) event. The data showed that DSC (differential scanning calorimetry) can detect the presence of crystalline CX-157 in the CX-157/PL90H (1:3; w/w) complex down to at least 5%.

The stability of RV and SD samples upon storage was analyzed. One RV sample was stored at 40° C. under 75% relative humidity (RH) in the open for 19 days. Another RV sample was stored at 25° C. under 60% relative humidity (RH) in the open for 19 days. One SD sample was stored at 40° C. under 75% relative humidity (RH) in the open for 19 days. Another SD sample was stored at 25° C. under 60% relative humidity (RH) in the open for 19 days. No crystalline CX-157 (Form A) was detected in the storage sample as shown in Table 7.

TABLE 7

Endothermic events

| Sample ID | Peaks (° C.) | Heat Fusion (uV · s/mg) |
|---|---|---|
| (RV, Time 0) | 154.8 | 4.86 |
| (RV, 25° C./60% RH/open, 19 days) | 155.3 | 5.09 |
| F-11 (RV, 40° C./75% RH/open, 19 days) | 155.5 | 6.02 |
| (SD, Time 0) | 152.4 | 7.07 |
| (SD, 25° C./60% RH/open, 19 days) | 153.6 | 7.08 |
| (SD, 40° C./75% RH/open, 19 days) | 155.2 | 7.43 |

No sign of formation of crystalline CX-157 was observed in the Intermediate Stability Samples (19 days at 25° C./60% RH/open and 40° C./75% RH/open). However, moisture uptake by both SD and RV complexes were detected.

Example 6

X-Ray Powder Diffraction (XRPD) as a Method to Detect Crystalline CX-157 in SD and RV Complexes
Method SD preparation of CX-157/PL90H and RV preparation of CX-157/PL90H were analyzed on the Bruker D8 Advance x-ray diffractometer with a LynxEye detector and Goble Mirrors. The conditions and instrumental settings were:

1.6 Kw power 2-theta range=4, 5-35

Step size=0.02 degrees

Time per step=0.5 s

Number of scans=1-2

Temperature=ambient ~25° C.

Cell=low background cell, silicon 511 face

Air scattering slit 0.1° divergence slit

The XRPD of the SD preparation of CX-157/PL90H showed significant crystalline character. In addition a second phase was likely present as manifest in the broad peak in the ~20-25° region and other background scattering. The XRPD of RV preparation of CX-157/PL90H showed similar trends, with perhaps higher crystallinity but similar diffuse scattering. Many of the peaks in the SD preparation pattern were observed in the relatively more crystalline RV preparation pattern.

The SD or RV samples (both TO and 40° C./75% RH open for 40 days) did not exhibit any peak that is characteristic of CX-157 (Form A), suggesting absence of crystalline CX-157 (Form A) in both CX-157/PL90H preparations. The SD preparation of CX-157/PL90H did not change XRPD pattern after exposure to 40° C./75% RH for 40 days, indicating a physically stable material with no sign of conversion to crystalline CX-157 (Form A).

Example 7

Composition of SD Preparation of CX-157/PL90H (1:3; w/w) Complex at 125 mg Strength The SD preparation of CX-157/PL90H (1:3; w/w) complex was formulated using microcrystalline cellulose, mannitol, crospovidone, and magnesium stearate in a variety of ratios. The A-1, B-1 and C-1 formulations shown in Table 8 provided a total mass of 1000 mg per pill to deliver 125 mg of CX-157. Formulation A-1 had no mannitol, formulation B-1 had no microcrystalline cellulose and formulation C-1 had a ratio of microcrystalline cellulose to mannitol of 6:5. All formulations had pharmaceutically acceptable appearance, weight, hardness and flow with no capping, punch sticking or fill weight problem.

TABLE 8

| Components | Composition of Formulation (mg/tablet) | | |
|---|---|---|---|
| | A-1 | B-1 | C-1 |
| CX-157/PL90H (1:3; w/w) | 500 (125 mg, CX-157) | 500 (125 mg, CX-157) | 500 (125 mg, CX-157) |
| Microcrystalline cellulose | 440 | 0 | 240 |
| Mannitol | 0 | 440 | 200 |
| Crospovidone | 50 | 50 | 50 |
| Magnesium Stearate | 10 | 10 | 10 |
| Total | 1000 | 1000 | 1000 |

Example 8

POLYMER SCREENING: Polymers were screened for their ability to stabilize CX-157 in an amorphous state. Spray dried dispersions (SDD) were prepared using a GEA-Niro SD Micro™ Spray Dryer (Niro Inc., Denmark). The Polymers screened were:

TABLE 9

| Component | Chemical Name |
|---|---|
| HPMCAS-M | Hydroxypropyl Methylcellulose Acetate Succinate |
| Eudragit L100-55 | 50:50 Copolymer of Methacrylic Acid and Ethyl Acrylate |
| copovidone, Plasdone S-630 | 60:40 Copolymer of Vinylpyrrolidone and Vinyl Acetate |
| povidone, Plasdone K-29/32 | Poly(vinylpyrrolidone) |

Spray dried dispersions were analyzed by differential scanning calorimetry (DSC) using a TA Instruments Q1000 modulated differential scanning calorimeter (TA Instruments, New Castle, Del.) to determine crystalline content. Three (3) out of the four (4) SDDs with 25% drug loading were amorphous: HPMCAS-M, copovidone and povidone (Examples 9-11). The SDD containing Eudragit L100-55 was crystalline at 25% drug loading. The SDDs were analyzed by DSC after stressing open sample containers at 40° C./75% RH for 65 h, and these three CX-157/Polymer SDDs remained amorphous.

DRUG LOADING EXPERIMENT: Two polymers, copovidone and povidone, were selected from the polymer screening experiments for further drug loading experiment. Six (6) spray dried dispersions (SDD) were prepared using a GEA-Niro SD Micro™ Spray Dryer. SDDs were prepared at 30, 35 and 40% drug loading.

Spray dried dispersions were analyzed by DSC to determine crystalline content. DSC results are shown below after production and after stressing open sample containers at 40° C./75% RH for 65 h:

TABLE 10

| Polymer | Drug Loading (w/w %) | DSC Result Immediately After Spray Drying | DSC Result After 65 h at 40° C./75% RH |
|---|---|---|---|
| copovidone | 25%[a] | Amorphous | Amorphous |
| | 30% | Amorphous | Amorphous |
| | 35% | Amorphous | Amorphous |
| | 40% | Amorphous | Amorphous |
| povidone | 25%[a] | Amorphous | Amorphous |
| | 30% | Amorphous | Amorphous |
| | 35% | Amorphous | Amorphous |
| | 40% | Crystalline | Crystalline |

[a]Samples prepared as part of polymer screening experiments; not repeated during drug loading experiment.

PSD-1 SPRAY DRYER EXPERIMENTS: Process development parameters, including nozzle/orifice size, atomization rate/pressure, and inlet and outlet gas temperature, were examined on the R&D PSD-1 spray dryer.

A preferred process from these studies was:

TABLE 11

| CX157 w/w % | 2.5 |
|---|---|
| copovidone w/w % | 7.5 |
| Acetone w/w % | 90 |
| Dryer Inlet Temperature, ° C. | 95 (90-120 allowable) |
| Dryer Outlet Temperature, ° C. | 52 (49-56 allowable) |
| Process Gas Flow, kg/h | 80 (75-90 allowable) |
| Atomization Pressure, bar | 1.0 (0.7-1.3 allowable) |

FLUID BED DRYING PROCESS: A secondary drying process using the Niro-Aeromatic MP-1 Fluid Bed Processor was developed to ensure that residual acetone levels meet the ICH guidelines. A drying curve is provided in FIG. 1.

The final drying conditions were determined to be:

TABLE 12

| Inlet Air Temperature, ° C. | 50 (35-60 allowable) |
|---|---|
| Airflow, CMH | 25 (20 to 100 allowable) |
| Filter Cleaning Interval, s | 60 (40-120 allowable) |

Example 9

1:3 CX-157:HPMCAS-M Spray Dried Dispersion

A solution of 2.5 g CX-157 (Albany Molecular Research Inc., Albany, N.Y.) and 7.5 g HPMCAS-M (Shin Etsu Chemical Co., Tokyo, Japan.) in 333.3 g of a 2:1 (w:w) acetone:methanol solvent mixture was prepared. This solution was spray dried using a GEA-Niro SD Micro™ Spray Dryer using heated Nitrogen as the drying gas. The CX-157/HPMCAS solution was atomized using a 0.5 mm two-fluid Schlick nozzle, and the atomizing gas pressure was 0.5 bar. The inlet temperature was approximately 85° C. and the outlet temperature was 55° C. The SDD product was collected in a cyclone collector with a small baghouse collecting all the fines. Secondary drying was performed in a vacuum oven for 12 h at 35-45° C. at reduced pressure between −25 to −30 in Hg.

Example 10

1:3 CX-157:Copovidone Spray Dried Dispersion

A solution of 2.5 g CX-157 (Albany Molecular Research Inc., Albany, N.Y.) and 7.5 g copovidone (International Specialty Products Inc., Wayne, N.J.) in 333.3 g of a 2:1 (w:w) acetone:methanol solvent mixture was prepared. This solution was spray dried using a GEA-Niro SD Micro™ Spray Dryer using heated Nitrogen as the drying gas. The CX-157/copovidone solution was atomized using a 0.5 mm two-fluid Schlick nozzle, and the atomizing gas pressure was 0.5 bar. The inlet temperature was approximately 85° C. and the outlet temperature was 55° C. The SDD product was collected in a cyclone collector with a small baghouse collecting all the fines. Secondary drying was performed in a vacuum oven for 12 h at 35-45° C. at reduced pressure between −25 to −30 in Hg.

Example 11

1:3 CX-157: Povidone Spray Dried Dispersion

A solution of 2.5 g CX-157 (Albany Molecular Research Inc., Albany, N.Y.) and 7.5 g povidone (International Specialty Products Inc., Wayne, N.J.) in 333.3 g of a 2:1 (w:w) acetone:methanol solvent mixture was prepared. This solution was spray dried using a GEA-Niro SD Micro™ Spray Dryer using heated Nitrogen as the drying gas. The CX-157/povidone solution was atomized using a 0.5 mm two-fluid Schlick nozzle, and the atomizing gas pressure was 0.5 bar. The inlet temperature was approximately 85° C. and the outlet temperature was 55° C. The SDD product was collected in a cyclone collector with a small baghouse collecting all the fines. Secondary drying was performed in a vacuum oven for 12 h at 35-45° C. at reduced pressure between −25 to −30 in Hg.

Example 12

25:75 CX-157: Copovidone Spray Dried Dispersion

A solution of 2.5 g CX-157 (Albany Molecular Research Inc., Albany, N.Y.) and 7.5 g copovidone (International Specialty Products Inc., Wayne, N.J.) in 90 g acetone was prepared. This solution was spray dried using a GEA-Niro SD Micro™ Spray Dryer using heated Nitrogen as the drying gas. The CX-157/copovidone solution was atomized using a 0.5 mm two-fluid Schlick nozzle, and the atomizing gas pressure was 0.5 bar. The inlet temperature was approximately 85° C. and the outlet temperature was 55° C. The SDD product was collected in a cyclone collector with a small baghouse collecting all the fines. Secondary drying was performed in a vacuum oven for 12 h at 35-45° C. at reduced pressure between −25 to −30 in Hg.

Example 13

35:65 CX-157: Copovidone Spray Dried Dispersion

A solution of 3.5 g CX-157 (Albany Molecular Research Inc., Albany, N.Y.) and 6.5 g copovidone (International Specialty Products Inc., Wayne, N.J.) in 90 g of acetone was prepared. This solution was spray dried using a GEA-Niro SD Micro™ Spray Dryer using heated Nitrogen as the drying gas. The CX-157/copovidone solution was atomized using a 0.5 mm two-fluid Schlick nozzle, and the atomizing gas pressure was 0.5 bar. The inlet temperature was approximately 85° C. and the outlet temperature was 55° C. The SDD product was collected in a cyclone collector with a small baghouse collecting all the fines. Secondary drying was performed in a vacuum oven for 12 h at 35-45° C. at reduced pressure between −25 to −30 in Hg.

Example 14

25:75 CX-157: Povidone Spray Dried Dispersion

A solution of 2.5 g CX-157 (Albany Molecular Research Inc., Albany, N.Y.) and 7.5 g povidone (International Specialty Products Inc., Wayne, N.J.) in 90 g of a 2:1 (w:w) acetone:methanol solvent mixture was prepared. This solution was spray dried using a GEA-Niro SD Micro™ Spray Dryer using heated Nitrogen as the drying gas. The CX-157/copovidone solution was atomized using a 0.5 mm two-fluid Schlick nozzle, and the atomizing gas pressure was 0.5 bar. The inlet temperature was approximately 85° C. and the outlet temperature was 55° C. The SDD product was collected in a cyclone collector with a small baghouse collecting all the fines. Secondary drying was performed in a vacuum oven for 12 h at 35-45° C. at reduced pressure between −25 to −30 in Hg.

Example 15

1:3 CX-157: Copovidone Spray Dried Dispersion

A solution of 1.25 kg CX-157 (Albany Molecular Research Inc., Albany, N.Y.) and 3.75 kg copovidone (International Specialty Products Inc., Wayne, N.J.) in 45 kg acetone was prepared. This solution was spray dried using a GEA-Niro PSD-1 Spray Dryer using heated Nitrogen as the drying gas. The CX-157/copovidone solution was atomized using a 1.0 mm two-fluid Schlick nozzle, and the atomizing gas pressure was 1.0 bar. The inlet temperature was approximately 95° C. (90-120° C. allowable range) and the outlet temperature was 52° C. (49-56° C. allowable range), and the process gas flow rate was 80 kg/h (75-90 kg/h allowable range). The SDD product was collected in a cyclone collector with a baghouse collecting all the fines.

Secondary drying was performed in a Niro-Aerometic MP-1 Fluid Bed Processor as a fluid bed dryer with a standard 21 L container. The product retention screen had a mesh size of 100 and the exhaust filter bags were 3 to 20 µm. During fluid bed drying of the SDD powder, the target inlet air temperature was 50° C. (35-60° C. allowable range), the airflow rate was 25 CMH (20-100 CMH allowable range), and the filter cleaning interval was 60 s (40-120 s allowable range).

Example 16

Enteric-Coated Sustained Release Tablet Formulation

| Enteric Capsules of 3-fluoro-7-(2,2,2-trifluoroethoxy)phenoxathiin 10,10-dioxide (60 mg/capsule) | |
|---|---|
| Materials | |
| Core | |
| Sucrose-starch nonpareils, 30-35 mesh | 134.15 mg |
| Sustained Release Active layer | |
| 3-fluoro-7-(2,2,2-trifluoroethoxy)phenoxathiin 10,10-dioxide | 60 mg |
| Sucrose | 25.72 mg |
| Hydroxypropylmethylcellulose | 12.89 mg |
| Separating layer | |
| Hydroxypropylmethylcellulose | 9.45 mg |
| Sucrose | 28.24 mg |
| Talc, 500 mesh | 50.21 mg |
| Enteric layer | |
| HPMCAS-LF | 65.66 mg |
| Triethyl citrate | 13.14 mg |
| Talc, 500 mesh | 39.66 mg |
| Finishing Layer | |
| Color mixture white (HPMC + titanium dioxide) | 43.02 mg |
| HPMC | 10.78 mg |
| Talc | Trace |

The active layer was built up by suspending 3-fluoro-7-(2,2,2-trifluoroethoxy)phenoxathiin 10,10-dioxide 25% w/w in a binder solution consisting of 6.4% w/w sucrose and 3.2% w/w hydroxypropylmethylcellulose (HPMC). The resulting suspension was then passed through a Coball Mill (Fryma Mashinen AG, Rheinfelden, Switzerland) Model MS-12 to reduce the particle size of the bulk drug. The milled suspension was applied to 1.5 kg of sucrose starch non-pareils in a fluid bed dryer fitted with a Wurster column. Upon completing the application of the desired quantity of active ingredient suspension, the core pellets were completely dried in the fluid bed dryer.

The separating layer which contains talc 12% w/w, sucrose 6.75% w/w and hydroxypropylmethylcellulose 2.25% w/w was then applied as an aqueous suspension to the active core pellets. Upon completing the application of the desired quantity of suspension, the pellets were completely dried in the fluid bed dryer.

The enteric coating aqueous suspension contained hydroxypropylmethylcellulose acetate succinate type LF 6% w/w, talc 1.8% w/w, triethyl citrate 1.2% w/w which is fully neutralized by the addition of 0.47% w/w ammonium hydroxide. This enteric coating suspension was applied to the separation layer coated pellets. Upon completing the application of the desired quantity of enteric coating suspension, the pellets were completely dried in the fluid bed dryer and a small quantity of talc was added to reduce static charge.

A finishing layer was then applied which contains color mixture white (comprised of titanium dioxide and hydroxypropylmethylcellulose) 8% w/w and hydroxypropylmethylcellulose 2% w/w. Upon completing the application of the desired quantity of color coating suspension, the pellets were completely dried in the fluid bed dryer and a small quantity of talc was added to reduce static charge. The resulting pellets were assayed for active content and filled into capsules to provide 60 mg of 3-fluoro-7-(2,2,2-trifluoroethoxy)phenoxathiin 10,10-dioxide.

Specific pharmacological responses observed may vary according to and depending on the particular active compound selected or whether there are present pharmaceutical carriers, as well as the type of formulation and mode of administration employed, and such expected variations or differences in the results are contemplated in accordance with practice of the present invention.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

Since modifications will be apparent to those of skill in this art, it is intended that this invention be limited only by the scope of the appended claims.

We claim:

1. A pharmaceutical product comprising
a mixture of substantially amorphous 3-fluoro-7-(2,2,2-trifluoroethoxy)phenoxathin 10,10-dioxide as a therapeutically active ingredient and a stabilizer.

2. The pharmaceutical product of claim 1, wherein the amount of 3-fluoro-7-(2,2,2-trifluoroethoxy)phenoxathin 10,10-dioxide by weight is about 40% or less relative to the amount of weight of 3-fluoro-7-(2,2,2-trifluoroethoxy)phenoxathin 10,10-dioxide plus stabilizer.

3. The pharmaceutical product of claim 1, wherein no more than 10%, 5%, 2%, 1% or 0.1% of the 3-fluoro-7-(2,2,2-trifluoroethoxy)phenoxathin 10,10-dioxide is crystalline.

4. The pharmaceutical product of claim 1, wherein the area under the curve (AUC) of 3-fluoro-7-(2,2,2-trifluoroethoxy)phenoxathin 10,10-dioxide determined in a bioavailability assay of the pharmaceutical product is at least about 2-fold the AUC of a crystalline form of 3-fluoro-7-(2,2,2-trifluoroethoxy)phenoxathin 10,10-dioxide, wherein the crystalline form of 3-fluoro-7-(2,2,2-trifluoroethoxy)phenoxathin 10,10-dioxide has a melting point at about 169-175° C., and wherein the mixture contains no more than about 2 parts by weight of 3-fluoro-7-(2,2,2-trifluoroethoxy)phenoxathin 10,10-dioxide per about 3 parts by weight of stabilizer.

5. The pharmaceutical product of claim 1, wherein 3-fluoro-7-(2,2,2-trifluoroethoxy)phenoxathin 10,10-dioxide is the sole active ingredient in the pharmaceutical product.

6. The pharmaceutical product of claim 1, further comprising at least one therapeutically active ingredient.

7. A unit dosage of 3-fluoro-7-(2,2,2-trifluoroethoxy)phenoxathiin 10,10-dioxide, comprising the pharmaceutical product as in claim 1, wherein the unit dosage contains at least 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 mg of 3-fluoro-7-(2,2,2-trifluoroethoxy)phenoxathiin 10,10-dioxide.

8. The unit dosage of claim 7, wherein the unit dosage is formulated for oral delivery.

9. A method of inhibiting monoamine oxidase-A (MAO-A) in a mammal identified as being in need of inhibition of MAO-A comprising
administering a therapeutically effective amount of the pharmaceutical product of claim 1, wherein the ratio of 3-fluoro-7-(2,2,2-trifluoroethoxy)phenoxathiin 10,10-dioxide to stabilizer ranges from about 2:3 to about 1:10.

10. A method of treating or preventing a psychiatric disorder or psychiatric disease comprising
administering a therapeutically effective amount of the pharmaceutical product of claim 1, wherein the ratio of 3-fluoro-7-(2,2,2-trifluoroethoxy)phenoxathiin 10,10-dioxide to stabilizer ranges from about 2:3 to about 1:10.

11. The method of claim 10, wherein the psychiatric disorder or psychiatric disease is selected from the group consisting of major depressive disorder, dysthymia, childhood depression, atypical depression, bipolar disorder, mania and hypomania, generalized anxiety disorder, social anxiety disorder, obsessive compulsive disorder, panic disorder, post-traumatic stress disorder, premenstrual dysphoric disorder, attention deficit disorder, panic disorder, anergic depression, and treatment-resistant depression.

* * * * *